(12) United States Patent
Emert-Sedlak et al.

(10) Patent No.: US 8,541,415 B2
(45) Date of Patent: Sep. 24, 2013

(54) TARGETING AN HIV-1 NEF-HOST CELL KINASE COMPLEX

(75) Inventors: Lori Emert-Sedlak, Cranberry Twp., PA (US); Toshiaki Kodama, Sunnyvale, CA (US); Billy W. Day, Pittsburgh, PA (US); Weixiang Dai, Morgantown, WV (US); Ronald P. Trible, Atlanta, GA (US); Thomas E. Smithgall, Wexford, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 165 days.

(21) Appl. No.: 12/988,501

(22) PCT Filed: May 14, 2009

(86) PCT No.: PCT/US2009/002996
§ 371 (c)(1),
(2), (4) Date: Apr. 18, 2011

(87) PCT Pub. No.: WO2009/139886
PCT Pub. Date: Nov. 19, 2009

(65) Prior Publication Data
US 2011/0190241 A1    Aug. 4, 2011

Related U.S. Application Data

(60) Provisional application No. 61/053,135, filed on May 14, 2008.

(51) Int. Cl.
*A01N 43/58* (2006.01)
*A01N 43/60* (2006.01)
*A61K 31/50* (2006.01)
*A61K 31/495* (2006.01)
*C07D 241/36* (2006.01)

(52) U.S. Cl.
USPC .......................................... 514/249; 544/356

(58) Field of Classification Search
None
See application file for complete search history.

(56) References Cited

FOREIGN PATENT DOCUMENTS

| WO | WO-2005/067546 | 7/2005 |
|---|---|---|
| WO | WO-2006/004658 | 1/2006 |
| WO | WO-2007/044729 | 4/2007 |
| WO | WO-2008/021389 | 2/2008 |
| WO | WO-2009/139886 | 11/2009 |

OTHER PUBLICATIONS

Alison L. Greenway et al., "HIV-1 Nef control of cell signalling molecules: multiple strategies to promote virus replication", J. Biosci., vol. 28, No. 3, Apr. 2003, 323-335.
Chien-Hui Hung et al., "HIV-1 Nef Assembles a Src Family Kinase-ZAP-70/Syk-PI3K Cascade to Downregulate Cell-Surface MCH-1", Cell Host & Microbe 1, 121-133, Apr. 2007.
International Search Report PCT/US2009/002996 dated Jan. 13, 2010.
Nicolas Faloppe et al., "Structure-Based Design of Novel Chk1 Inhibitors: Insights into Hydrogen Bonding and Protein-Ligand Affinity", J. Med. Chem. 2005, 48, 4332-4345.

*Primary Examiner* — Jeffrey Murray
(74) *Attorney, Agent, or Firm* — Foley & Lardner

(57) ABSTRACT

Drug candidates for inhibition of HIV-I replication can target Src family kinases (SFK), such as Hck, that interact with Nef protein of the virus. Compounds characterized by such inhibitory activity were identified via an assay for kinase activity of an SFK in a Nef:SFK complex. Illustrative of inhibitors identified using the kinase assay are various 2,3-diaminoquinoxolines and furo[2,3-d]pyrimidines. The inventive inhibitors were found to arrest HIV-I viral replication in vitro.

5 Claims, 8 Drawing Sheets

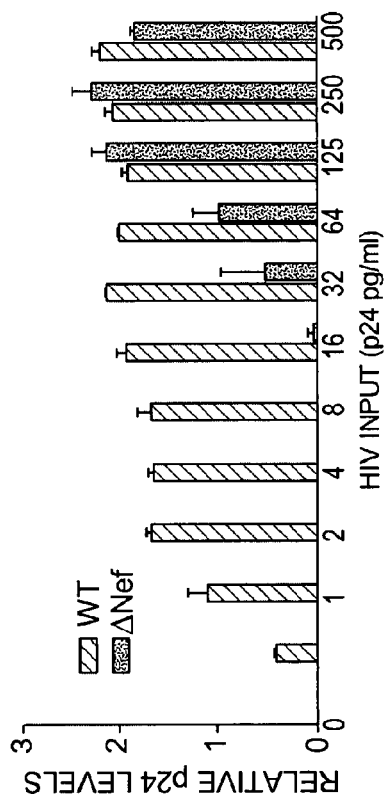
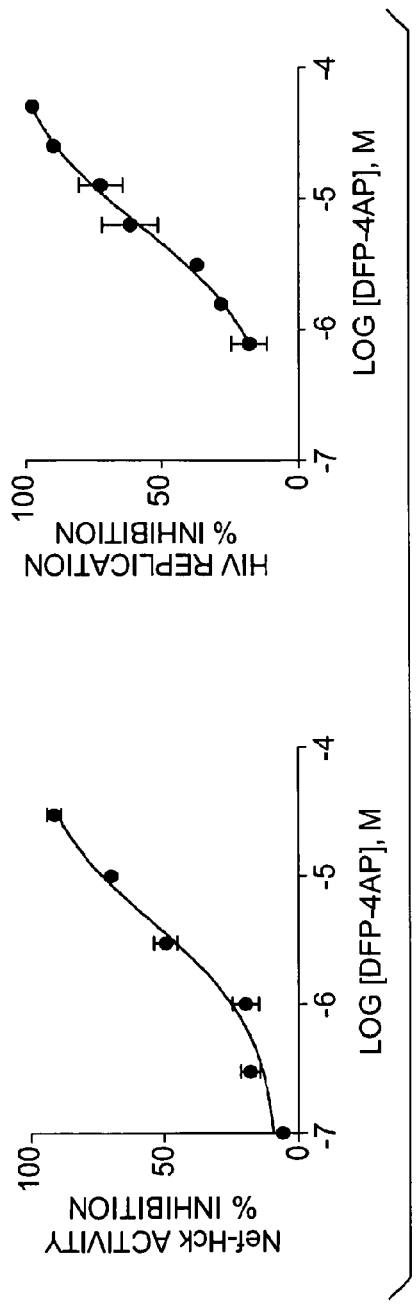
FIG. 5A
FIG. 5B

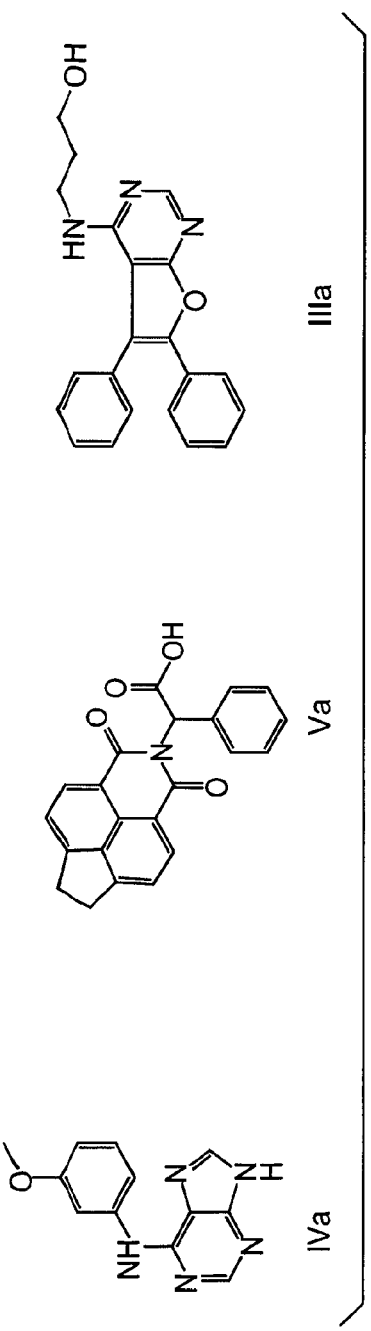
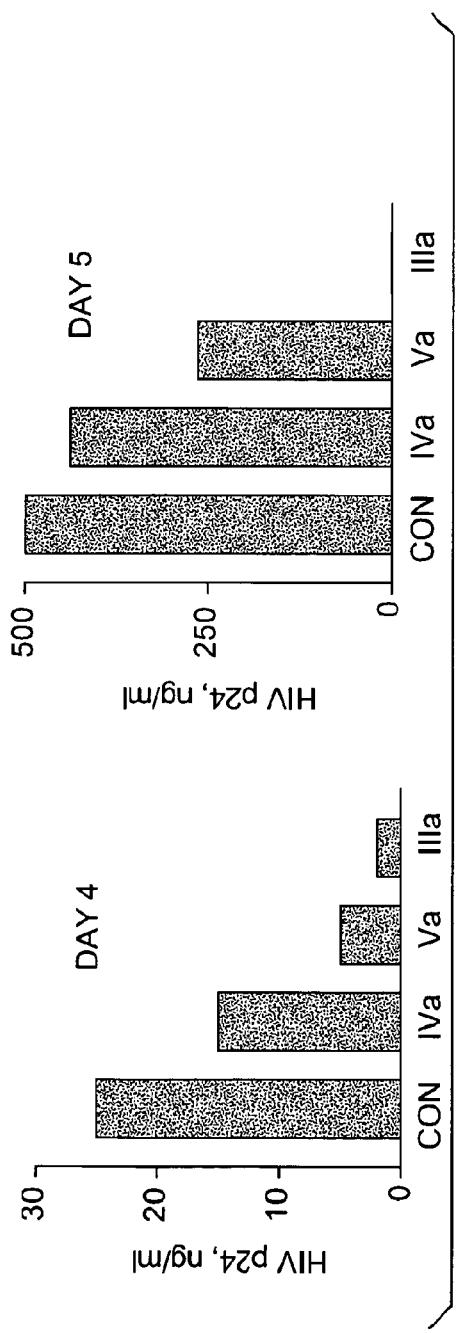
FIG. 6A
FIG. 6B

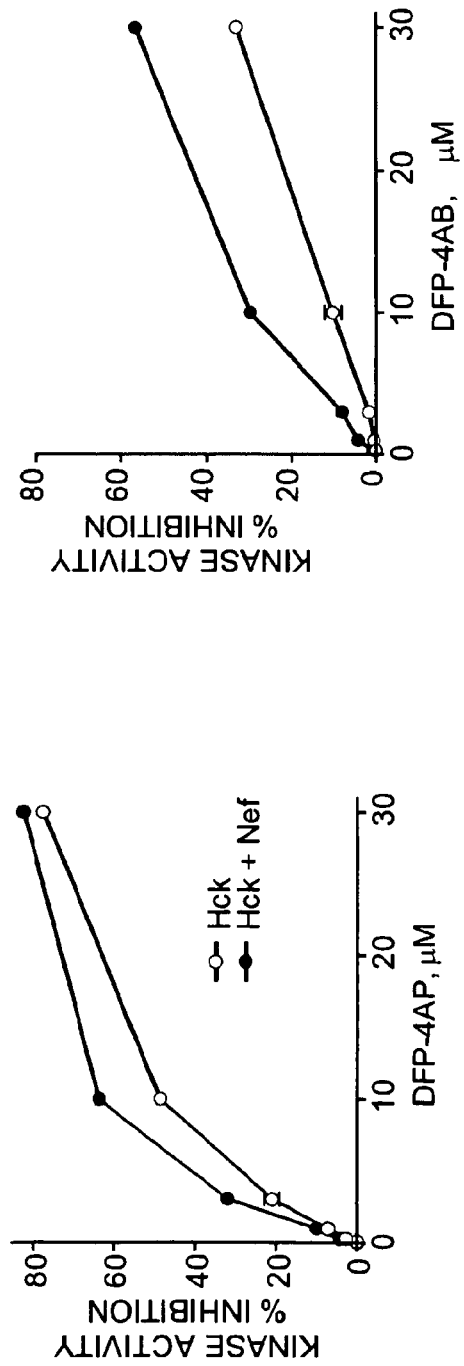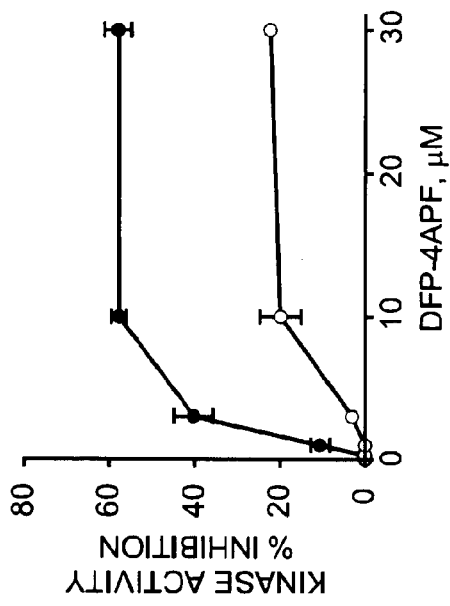

TARGETING AN HIV-1 NEF-HOST CELL KINASE COMPLEX

CROSS-REFERENCE TO RELATED PATENT APPLICATIONS

This application claims priority from U.S. Provisional Application Ser. No. 61/053,135, filed May 14, 2008, incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 17, 2013, is named 076333-0708_SL.txt and is 15,240 bytes in size.

STATEMENT REGARDING FEDERALLY SPONSORED RESEARCH

This invention was funded by NIH AI57083 and NIH CA81398 grants. The United States government has certain rights in the invention.

BACKGROUND OF THE INVENTION

The present invention relates generally to inhibition of protein activity, and in particular kinase activity, and compounds and assays for measuring such inhibition useful for identifying novel inhibitors of kinas activity. In particular, the present invention relates Nef protein and inhibition of its interaction and complexes comprising Nef, with other cellular components as described herein and known in the art.

The information provided herein is intended solely to assist the understanding of the reader. None of the information provided nor references cited is admitted to be prior art to the present invention. Each of the references cited herein is incorporated in its entirety and for all purposes.

The HIV-1 nef gene encodes a small myristoylated accessory protein Nef, having NCBI Locus CAA41585 (SEQ ID NO: 1), which protein is required for optimal viral replication and AIDS pathogenesis (Fackler, O. T. and Baur, A. S., 2002, *Immunity.* 16:493-497; Geyer, M., Fackler, O. T. and Peterlin, B. M., 2001, *EMBO Rep.* 2:580-585). It is understood that the term "NCBI Locus" refers to a unique alphanumeric identifier given to a sequence deposited with the National Center for Biotechnology Information. Deletion of nef from the HIV-related simian immunodeficiency virus (SIV) prevents AIDS-like disease progression in rhesus macaques (Kestler, H. W., III, Ringler, D. J., Mori, K., Panicali, D I., Sehgal, P. K., Daniel, M. D. and Desrosiers, R. C., 1991, *Cell* 65:651-662). In addition, expression of the nef gene alone is sufficient to induce an AIDS-like syndrome in transgenic mice very similar to that observed upon expression of the complete HIV-1 provirus therein (Hanna, Z., Kay, D. G., Cool, M., Jothy, S., Rebai, N. and Jolicoeur, P., 1998, *J. Virol.* 72:121-132; Hanna, Z., Kay, D. G., Rebai, N., Guimond, A., Jothy, S. and Jolicoeur, P., 1998, *Cell* 95:163-175). In humans, nef sequence variability and function correlate with HIV disease progression over the course of infection (Carl, S., Greenough, T. C., Krumbiegel, M., Greenberg, M., Skowronski, J., Sullivan, J. L. and Kirchhoff, F., 2001, *J. Virol.* 75:3657-3665; Kirchhoff, F., Easterbrook, P. J., Douglas, N., Troop, M., Greenough, T. C., Weber, J., Carl, S., Sullivan, J. L. and Daniels, R. S., 1999, *J. Virol.* 73:5497-5508). Indeed, long-term non-progressive HIV infection has been associated with nef-defective strains of HIV in some cases (Deacon, N. J., Tsykin, A., Solomon, A., Smith, K., Ludford-Menting, M., Hooker, D. J., McPhee, D. A., Greenway, A. L., Ellett, A., Chatfield, C., 1995, *Science* 270:988-991; Kirchhoff, F., Greenough, T. C., Brettler, D. B., Sullivan, J. L. and Desrosiers, R. C., 1995, *N. Engl. J. Med.* 332:228-232). Thus, several studies identify the HIV-1 Nef protein as a key molecular determinant of AIDS and related conditions (e.g., AIDS-related syndrome).

Because Nef lacks any known intrinsic enzymatic or biochemical function, it is believed that Nef exploits multiple host cell signaling pathways to optimize conditions for viral replication and AIDS progression (Fackler, O. T. and Baur, A. S., Id.; Greenway, A. L., Holloway, G., McPhee, D. A., Ellis, P., Cornall, A. and Lidman, M., 2003, *J. Biosci.* 28:323-335; Joseph, A. M., Kumar, M. and Mitra, D., 2005, *Curr. HIV. Res.* 3:87-94; Piguet, V. & Trono, D., 1999, *Reviews in Medical Virology,* 9:111-120; Renkema, G. H. & Saksela, K., 2000, *Front Biosci.* 5:D268-D283). Indeed, Nef binding influences several classes of signaling molecules, including immune receptors, trafficking proteins, guanine nucleotide exchange factors, and protein kinases (Arold, S. T. & Baur, A. S., 2001, *Trends Biochem. Sci.* 26:356-363; Geyer, M., et al., 2001, Id.). These Nef-mediated interactions enhance viral replication and contribute to immune evasion as well as survival of infected cells (Briggs, S. D. et al., 2001, *J. Biol. Chem.* 276:25605-25611; Choi, H.-J. & Smithgall, T. E., 2004, *Biol. Chem.* 279:51668-51696; Geleziunas, R., Xu, W., Takeda, K., Ichijo, H. & Greene, W. C., 2001, *Nature* 410:834-838).

The prior art identifies the Src family kinases (SFKs), a group of non-receptor protein-tyrosine kinases that control cell growth, differentiation, and survival (Parsons, S. J. & Parsons, J. T., 2004, *Oncogene* 23:7906-7909; Thomas, S. M. & Brugge, J. S., 1997, *Annu. Rev. Cell Dev. Biol.* 13:513-609), as key molecular targets for Nef (Greenway, A. L., Holloway, G., McPhee, D. A., Ellis, P., Cornall, A. and Lidman, M., 2003, *J. Biosci.* 28:323-335; Renkema, G. H. and Saksela, K., 2000, *Front Biosci.* 5:D268-D283). Accordingly, members of the Src family of non-receptor protein-tyrosine kinases represent an important class of Nef target proteins. Nef binds to the Src homology 3 (SH3) domains from the Src family members Fyn, Hck, Lck, Lyn and c-Src, all of which are expressed in HIV-1 target cells (Saksela, K., Cheng, G. & Baltimore, D., 1995, *EMBO J.* 14:484-491; Arold, S. et al. 1997, *Structure* 5:1361-1372; Choi, H. J. & Smithgall, T. E., 2004, *J. Mol. Biol.* 343:1255-1268; Arold, S. et al., 1998, *Biochemistry* 37:14683-14691). It is believed that Nef activates c-Src and Lyn through a similar mechanism, suggesting that Nef-mediated Src family kinase activation is a common feature of HIV-infected cells (Trible, R. P., Emert-Sedlak, L. & Smithgall, T. E., 2006, *J. Biol. Chem.* 281:27029-27038.

The SFK Hck is a Src family member expressed in macrophages that binds strongly to Nef via an SH3-mediated interaction (Arold, S., et al., Id.; Lee, C. H., Leung, B., Lemmon, M. A., Zhong, J., Cowburn, D., Kuriyan, J. and Saksela, K., 1995, *EMBO J.* 14:5006-5015). Nef induces constitutive activation of Hck through a mechanism that involves displacement of the SH3 domains negative regulatory interaction with the catalytic domain (Moarefi, I. et al., 1997, *Nature* 385:650-653; Briggs, S. D., Sharkey, M., Stevenson, M. & Smithgall, T. E., 1997, *J. Biol. Chem.* 272:17899-17902). Nef binding leads to constitutive Hck activation (Briggs, S. D., et al., Id.; Lerner, E. C. & Smithgall, T. E., 2002, *Nat. Struct. Biol.* 9:365-369; Moarefi, I., LaFevre-Bernt, M., Sicheri, F., Huse, M., Lee, C. H., Kuriyan, J. and Miller, W. T., 1997, *Nature* 385:650-653; Trible, R. P., Emert-Sedlak, L. and Smithgall, T. E., 2006, *J. Biol. Chem.* 281:27029-27038), which may be important for macrophage survival (Briggs, S. D., Scholtz, B., Jacque, J. M., Swingler, S., Stevenson, M. and Smithgall, T. E., 2001, *J. Biol. Chem.* 276:25605-25611; Choi, H. J. & Smithgall, T. E., 2004, *J. Biol. Chem.* 279: 51688-51696) and productive infection by M-tropic HIV (Komuro, I., Yokota, Y., Yasuda, S., Iwamoto, A. and Kagawa, K. S., 2003, *Exp. Med.* 198:443-453). Strikingly, transgenic mice expressing a Nef mutant lacking a highly conserved PxxPxR motif essential for activation of Hck and other SFKs showed no evidence of AIDS-like disease (Hanna, Z., Weng, X., Kay, D. G., Poudrier, J., Lowell, C. and Jolicoeur, P., 2001, *J. Viral.* 75:9378-9392). Furthermore, when the Nef-transgenic mice were crossed into a hck-null background, appearance of AIDS-like phenotype was delayed and mortality was reduced (Hanna, Z., et al., Id.). While not dictating adherence to a particular theory, these observations support an essential role for Nef:SFK interactions in AIDS pathogenesis and suggest that small molecules targeted to Nef:SFK complexes may represent new leads for anti-HIV therapy. It is understood that the terms "Nef:SFK," "Nef:SFK complex" and the like refer to the complex formed between Nef and an SFK, for example, Nef:Hck.

To reiterate, lack of a catalytic function makes analyses of the interaction of Nef with small molecule inhibitors by a variety of approaches, such as high-throughput screening (HTS) approaches, problematic. Accordingly, the present invention provides assays suitable to identify inhibitors of Nef:SFK (e.g., Nef-Hck) signaling despite the lack of a catalytic function for Nef.

The screening assays of the present inventionare useful for identifying inhibitors of kinase activity of Nef:SFK complex. The invention further provides compounds useful as drugs resulting from the use of such assays.

SUMMARY OF THE INVENTION

By the present invention, are provided compounds that inhibit the kinase activity of a Nef:SFK complex, for example, without limitation the Nef:Hck complex, which compounds were identified by screening assays described herein. The terms "derivative thereof," "mutant thereof" and like terms in the context of proteins contemplated by the present invention (e.g., Nef, Hck, Hck-YEEI (SEQ ID NO: 4), and the like) refers to mutation (e.g., deletion, addition, and/or replacement of amino acids) which mutation does not eliminate the utility of the resulting proteins in the assays described and provided herein. Thus, the "mutation" contemplated by the present invention includes conserved amino acid replacement with respect to charge type (e.g., Glu/Asp or Lys/Arg interchange and the like), lipophilicity (e.g., Leu/Ile interchange and the like), side chain bulk (e.g., Phe/Tyr interchange and the like), and other metrics that are well known to protein chemistry. "Mutation" also contemplates deletion and insertion of amino acid residues, likewise well known in the field. "Mutation" further encompasses specific replacement of residues, e.g., the replacement of the YEEI tetrapeptide (SEQ ID NO: 5) to afford Hck-YEEI (SEQ ID NO: 4), as described herein, and the like. Pursuant to this invention, mutants of proteins, such as Nef, Hck and Hck-YEEI (SEQ ID NO: 4), display homology, as measured by metrics well known in the art, in the range 80-100% with respect to wild-type. In some embodiments, the homology is 80, 85, 90, 91, 92, 93, 94, 95, 96, 97, 98, 99% or even greater, as measured by amino acid identity over the full length of the mutant and wild-type proteins. In some embodiments, the homology is 80, 85, 90, 91, 92, 93, 94, 95, 96, 97, 98, 99% or even greater, as measured by conservative amino acid replacement over the full length of the mutant and wild-type proteins. In the context of non-protein organic compounds, for example, organic groups and functionalities as described here, the term "derivative" refers to groups or functionalities having undergone substitution as described herein.

Accordingly, in one aspect, the invention provides compounds having the structure of Formula I,

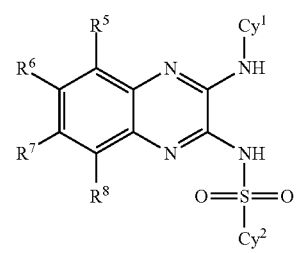

I wherein:
Cy$^1$ and Cy$^2$ are independently selected from the group consisting of optionally substituted aryl and optionally substituted heteroaryl;
R$^5$, R$^6$, R$^7$, and R$^8$ are independently selected from the group consisting of hydrogen, halogen, optionally substituted alkyl, —OR$^{11}$, —SR$^{11}$, —NR$^{12}$R$^{13}$, —C(Z)NR$^{12}$R$^{13}$, and —C(Z)R$^{14}$;
R$^{11}$ is selected from the group consisting of optionally substituted alkyl, optionally substituted cycloalkyl, optionally substituted heterocycloalkyl, optionally substituted aryl, optionally substituted arylalkyl, optionally substituted heteroaryl, and optionally substituted heteroarylalkyl;
R$^{12}$ and R$^{13}$ are independently selected from the group consisting of hydrogen, optionally substituted alkyl, optionally substituted cycloalkyl, optionally substituted heterocycloalkyl, optionally substituted aryl, optionally substituted arylalkyl, optionally substituted heteroaryl, and optionally substituted heteroarylalkyl, or
R$^{12}$ and R$^{13}$ combine to form a mono-carbocyclic or mono-heterocyclic 5- or 6-membered ring system;
R$^{14}$ is selected from the group consisting of optionally substituted alkyl, optionally substituted cycloalkyl, optionally substituted heterocycloalkyl, optionally substituted aryl, optionally substituted arylalkyl, optionally substituted heteroaryl, and optionally substituted heteroarylalkyl; and
Z is O or S.

In another aspect, the invention provides compounds having the structure of Formula III,

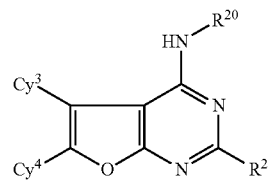

III wherein:
Cy$^3$ and Cy$^4$ are independently selected from the group consisting of optionally substituted aryl and optionally substituted heteroaryl;

R² is selected from the group consisting of hydrogen, halogen, and optionally substituted alkyl; and R²⁰ is selected from the group consisting of hydrogen, optionally substituted alkyl, optionally substituted aryl, optionally substituted arylalkyl, optionally substituted heteroaryl, and optionally substituted heteroarylalkyl.

In another aspect, the invention provides the use of inhibitors according to Formulae I or III to treat HIV-1 in a subject, which method comprises the following steps: (a) identifying a subject infected with HIV-1, and (b) administering to the subject a compound of Formula I or Formula III.

BRIEF DESCRIPTION OF THE DRAWINGS

FIG. 5: Inhibition of Nef-induced Hck activation and HIV-1 replication by 3-(5,6-diphenylfuro[2,3-d]pyrimidin-4-ylamino)propan-1-ol (DFP-4AP). (A). Measurement of Nef-dependence of HIV-1 replication in U87MG cells. Cells were infected with wild-type HIV strain NL4-3 (WT) or a mutant that fails to express Nef (ΔNef) over the range of viral titers shown. The ability of DFP-4AP to inhibit either HIV-1 strain was determined by measuring the relative HIV p24 levels at day 4 using ELISA. (B). Measurement of inhibition of Nef-induced Hck activation by DFP-4AP. The Nef:Hck complex was assayed in vitro with a peptide substrate in the presence of DFP-4AP over the range of concentrations (shown). Each concentration was assayed in triplicate and data expressed as percent inhibition relative to control reactions run in the absence of compound. The data were best-fit by non-linear regression analysis, yielding an IC$_{50}$ value of 4 μM. (C). Inhibition of HIV-1 replication by DFP. U87MG cells were infected with HIV strain NL4-3 in the presence of DFP-4AP over the range of concentrations (shown). Release of viral p24 was determined by ELISA 5 days later. The data were best-fit by non-linear regression analysis, yielding an IC$_{50}$ value of 6 μM.

FIG. 6: Nef:Hck kinase inhibitors block HIV-1 replication in cell culture. (A). Structures of confirmed hits obtained from the Nef:Hck-YEEI (SEQ ID NO: 4) inhibitor screen. Compound 3 is DFP-4-AP. (B). Nef:Hck kinase inhibitors block HIV-1 replication in cell culture. HIV replication assay was performed in U87MG cells which were infected with HIV strain NL4-3 in the presence of the compounds shown in 6A at 5 μM or with the DMSO (carrier solvent alone) as control (Con). Release of viral p24 was determined by ELISA after 4 (left) and 5 (right) days of infection.

FIG. 7: Selective in vitro inhibition of Nef-induced Hck activation by different diphenylfuro-pyrimidines analogs. The kinase activity of the Nef:Hck complex as well Hck alone were assayed in vitro with a peptide substrate in the presence of DFP-4AP and the three analogs shown in Scheme 1, over the concentration range shown. Each concentration was assayed in triplicate and data are expressed as percent inhibition relative to control run in the absence of compound. (A) 3-(5,6-diphenylfuro[2,3-d]pyrimidin-4-ylamino)propan-1-ol (DFP-4AP). (B) 3-(5,6-diphenylfuro[2,3-d]pyrimidin-4-ylamino)butan-1-ol (DFP-4AB). (C) N-(3-(furan-2-yl)propyl) 5,6-diphenylfuro[2,3-d]pyrimidin-4-amine (DFP-4APF).

DETAILED DESCRIPTION OF THE INVENTION

Figure 1:
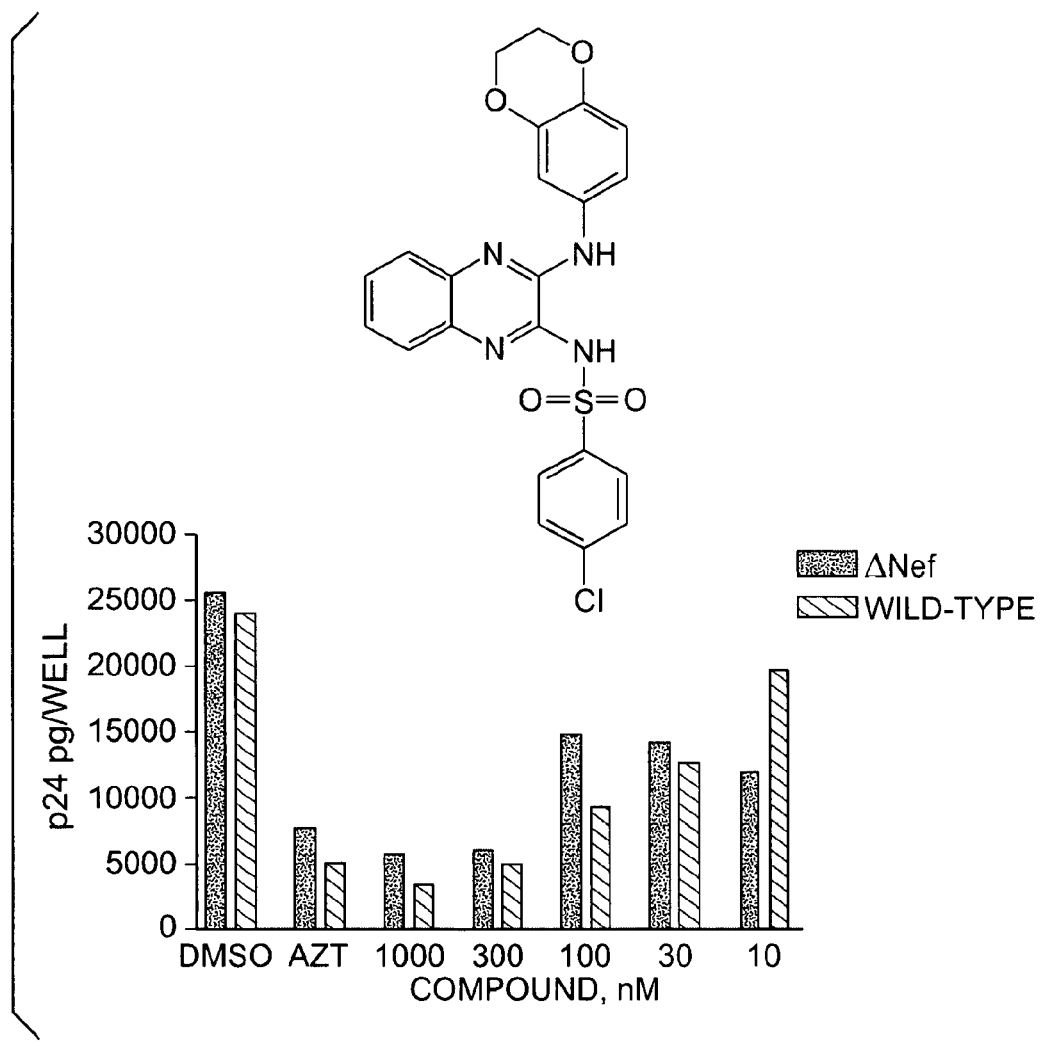
FIG. 1: Inhibition of replication of pseudotyped NL43 HIV-1 by 4-chloro-N-(3-(2,3-dihydrobenzo[1,4]dioxin-6-ylamino)quinoxalin-2-yl)benzenesulfonamide.

Compounds of the present invention may have asymmetric centers and may occur, except when specifically noted, as mixtures of stereoisomers or as individual diastereomers, or enantiomers, with all isomeric forms being contemplated by the present invention. Compounds of the present invention embrace all conformational isomers, including, for example, cis- or trans-conformations. Compounds of the present invention may also exist in one or more tautomeric forms, including both single tautomers and mixtures of tautomers.

Each of the terms "halogen," "halide," and "halo" refers to —F, —Cl, —Br, or —I.

"Alkyl" refers to straight, branched chain, or cyclic hydrocarbyl groups including from 1 to about 20 carbon atoms. Alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH₃)₂, —CH(CH₃)(CH₂CH₃), —CH(CH₂CH₃)₂, —C(CH₃)₃, —C(CH₂CH₃)₃, —CH₂CH(CH₃)₂, —CH₂CH(CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)₂, and the like. Thus, alkyl groups include primary alkyl groups, secondary alkyl groups, and tertiary alkyl groups. Preferred alkyl groups include alkyl groups having from 1 to 10 carbon atoms while even more preferred such groups have from 1 to 5 carbon atoms.

The phrase "substituted alkyl" refers to alkyl substituted at 1 or more, e.g., 1, 2, 3, 4, 5, or even 6 positions, in which substituents are attached at any available atom to produce a stable compound, with substitution as described herein. "Optionally substituted alkyl" refers to alkyl or substituted alkyl.

The term "cycloalkyl" refers to saturated or unsaturated non-aromatic monocyclic, bicyclic or tricyclic carbon ring systems of 3-10, more preferably 3-6, ring members per ring, such as cyclopropyl, cyclopentyl, cyclohexyl, adamantyl, and the like.

The phrase "substituted cycloalkyl" refers to cycloalkyl substituted at 1 or more, e.g., 1, 2, 3, or even 4 positions, in which substituents are attached at any available atom to produce a stable compound, with substitution as described herein. "Optionally substituted cycloalkyl" refers to cycloalkyl or substituted cycloalkyl.

The terms "alkylene" and "substituted alkylene" refer to divalent alkyl and divalent substituted alkyl, respectively. Examples of alkylene include without limitation, ethylene (—$CH_2$—$CH_2$—). "Optionally substituted alkylene" refers to alkylene or substituted alkylene.

"Alkene" refers to straight, branched chain, or cyclic hydrocarbyl groups including from 2 to about 20 carbon atoms having at least one, preferably 1-3, more preferably 1-2, most preferably one, carbon to carbon double bond. "Substituted alkene" refers to alkene substituted at 1 or more, e.g., 1, 2, 3, 4, 5, or even 6 positions, in which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

The term "aryl," alone or in combination refers to a monocyclic or bicyclic ring system containing aromatic hydrocarbons such as phenyl or naphthyl, which may be optionally fused with a cycloalkyl of preferably 5-7, more preferably 5-6, ring members.

A "substituted aryl" is an aryl that is independently substituted with one or more, preferably 1, 2, 3, 4 or 5, also 1, 2, or 3 substituents, also 1 substituent, attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heteroarylene" refers to divalent heteroaryl, and "substituted heteroarylene" refers to divalent substituted heteroaryl. "Optionally substituted heteroarylene" refers to heteroarylene or substituted heteroarylene.

"Heterocycloalkyl" means a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl or heterocycloalkyl that is substituted with 1 to 3 substituents, e.g., 1, 2 or 3 substituents, attached at any available atom to produce a stable compound, wherein the substituents are as described herein.

"Heteroalkyl" means a saturated or unsaturated alkyl group having from 1 to about 20 carbon atoms, preferably 1 to 10 carbon atoms, more preferably 1 to 6 carbon atoms, even more preferably 1 to 3 carbon atoms, in which from 1 to 3 carbon atoms are replaced by heteroatoms of O, S or N. Heteroalkyl is also intended to include oxidized S or N, such as sulfinyl, sulfonyl and N-oxide of a tertiary ring nitrogen. The point of attachment of the heteroalkyl substituent is at an atom such that a stable compound is formed. Examples of heteroalkyl groups include, but are not limited to, N-alkylaminoalkyl (e.g., $CH_3NHCH_2$—) N,N-dialkylaminoalkyl (e.g., $(CH_3)_2NCH_2$—), and the like.

"Heteroalkylene" refers to divalent heteroalkyl. The term "optionally substituted heteroalkylene" refers to heteroalkylene or heteroalkylene that is substituted with 1 to 3 substituents, e.g., 1, 2 or 3 substituents, attached at any available atom to produce a stable compound, wherein the substituents are as described herein.

"Heteroalkene" means a saturated or unsaturated alkyl group having from 1 to about 20 carbon atoms, preferably 1 to 10 carbon atoms, more preferably 1 to 6 carbon atoms, even more preferably 1 to 3 carbon atoms, in which from 1 to 3 carbon atoms are replaced by heteroatoms of O, S or N, and having at least one, preferably 1-3, more preferably 1-2, most preferably one, carbon to carbon double bond or carbon to heteroatom double bond.

"Heteroalkenylene" refers to divalent heteroalkene. The term "optionally substituted heteroalkenylene" refers to heteroalkenylene or heteroalkenylene that is substituted with 1 to 3 substituents, e.g., 1, 2 or 3 substituents, attached at any available atom to produce a stable compound, wherein the substituents are as described herein.

"Arylalkyl" refers to a moiety of structure —$R^a$—$R^b$, wherein $R^a$ is optionally substituted alkylene and $R^{13}$ is aryl, as define herein. "Optionally substituted arylalkyl" means arylalkyl or arylalkyl wherein the aryl functionality is substituted with 1 to 3 substituents, e.g., 1, 2 or 3 substituents, attached at any available atom to produce a stable compound, wherein the substituents are as described herein.

"Heteroarylalkyl" refers to a moiety of structure —$R^a$-$R^c$, wherein $R^a$ is optionally substituted alkylene and $R^c$ is heteroaryl, as define herein. "Optionally substituted heteroarylalkyl" means heteroarylalkyl or heteroarylalkyl wherein the heteroaryl functionality is substituted with 1 to 3 substituents, e.g., 1, 2 or 3 substituents, attached at any available atom to produce a stable compound, wherein the substituents are as described herein.

Moieties of the present invention may be substituted with various atoms or functionalities as described herein. As used here, "substitution" denotes an atom or group of atoms that has been replaced with another atom or group of atoms (i.e., substituent), and includes all levels of substitution, e.g. mono-, di-, tri-, tetra-, penta-, or even hex-substitution, where such substitution is chemically permissible. Substitutions can occur at any chemically accessible position and on any atom, such as substitution(s) on carbon and any heteroatom, preferably oxygen, nitrogen, or sulfur. For example, substituted moieties include those where one or more bonds to a hydrogen or carbon atom(s) contained therein are replaced by a bond to non-hydrogen and/or non-carbon atom(s). Substitutions can include, but are not limited to, a halogen atom such as F, Cl, Br, and I; an oxygen atom in groups such as hydroxyl groups, alkoxy groups, aryloxy groups, ethers, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

Specific examples of substituents contemplated by the present invention include without limitation, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR, —SR, —OC(O)R, —OC(S)R, —C(O)R, —C(S)R, —C(O)OR, —C(S)OR, —S(O)R, —S(O)$_2$R, —C(O)NHR, —C(S)NHR, —C(O)NRR, —C(S)NRR, —S(O)$_2$NHR, —S(O)$_2$NRR, —C(NH)NHR, —C(NH)NRR, —NHC(O)R, —NHC(S)R, —NRC(O)R, —NRC(S)R, —NHS(O)$_2$R, —NRS(O)$_2$R, —NHC(O)NHR, —NHC(S)NHR, —NRC(O)NH$_2$, —NRC(S)NH$_2$, —NRC(O)NHR, —NRC(S)NHR, —NHC(O)NRR, —NHC(S)NRR, —NRC(O)NRR, —NRC(S)NRR, —NHS(O)$_2$NHR, —NRS(O)$_2$NH$_2$, —NRS(O)$_2$NHR, —NHS(O)$_2$NRR, —NRS(O)$_2$NRR, —NHR, —NRR, where R at each occurrence is independently H, optionally substituted alkyl, optionally substituted aryl, or optionally substituted heteroaryl. Accordingly, substitutions can, in turn, be substituted. Also contemplated is substitution with an optionally substituted hydrocarbyl moiety containing one or more of the following chemical functionalities: —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O, —O—S(O)$_2$—NR—, —O—S(O)—, —O—S(O)—O—, O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—, where R is at each occurrence is independently H, optionally substituted alkyl, optionally substituted aryl, or optionally substituted heteroaryl.

Assays for Nef:SFK Kinase Activity

In certain embodiments the present invention contemplates methods of screening for an inhibitor of kinase activity of a Nef:SFK complex, the Nef:SFK complex comprises Nef (SEQ ID NO: 1) or mutant thereof and Hck (SEQ ID NO: 3) or mutant thereof. Without wishing to be bound by any theory, it is believed that Hck and other Src family kinases can adopt an inactive conformation in vivo as a result of phosphorylation of a conserved tyrosine residue within the C-terminal tail (Boggon, T. J. & Eck, M. J., 2004, *Oncogene* 23:7918-7927). This regulatory phosphorylation event is believed to require an independent kinase (e.g., Csk, SEQ ID NO: 2). Accordingly, to recapitulate this aspect of SFK regulation with respect to the adoption of an inactive conformation in the assays provided by the present invention, there was expressed and purified a form of Hck with a modified C-terminal tail (Hck-YEEI, SEQ ID NO: 4) previously shown to adopt the inactive kinase conformation independently of Csk (Schindler, T. et al., 1999, *Mol. Cell* 3:639-648). As known in the art, "Hck-YEEI" (SEQ ID NO: 4) refers to Hck having the tetrapeptide YEEI (i.e., Tyr-Glu-Glu-Ile) (SEC, ID NO: 5) at the C-terminal, replacing YQQQ (i.e., Tyr-Gln-Gln-Gln) (SEQ ID NO: 6) in wild-type Hck (SEQ ID NO: 3). Accordingly, the present invention provides an assay for Nef:Hck complex kinase activity comprising Nef or mutant thereof and Hck-YEEI (SEQ ID NO: 4) or mutant thereof. In certain embodiments, the Nef:Hck complex comprises Nef and Hck-YEEI (SEQ ID NO: 4).

Also provided is a high-throughput Nef:SFK assay system for screening an inhibitor of Nef:SFK complex kinase activity.

In vivo Yeast Assay for Nef:SFK Kinase Activity

In some embodiments of methods of screening for an inhibitor of kinase activity of a Nef:SFK complex, the Nef:SFK assay system is a cellular assay system comprising an engineered yeast cell, wherein the engineered yeast cell expresses Nef or mutant thereof and an SFK or mutant thereof, and wherein the determination of kinase activity comprises monitoring the growth of the yeast, wherein growth of the yeast indicates inhibition of kinase activity. The term "engineered" in the context of yeast cells refers to the result of incorporation of additional genetic material into the yeast, as well known in the art, for example without limitation, ectopic expression of active c-Src in yeast as described herein.

Without wishing to be bound by any theory, it is believed that HIV-1 Nef binds to Hck and induces the constitutive activation thereof in yeast and mammalian cells (Briggs, S. D., Scholtz, B., Jacque, J. M., Swingler, S., Stevenson, M. and Smithgall, T. E., 2001, *J. Biol. Chem.* 276:25605-25611; Briggs, S. D., Sharkey, M., Stevenson, M. and Smithgall, T. E., 1997, *J. Biol. Chem.* 272:17899-17902; Choi, H. J. and Smithgall, T. E., 2004, *J. Mol. Biol.* 343:1255-1268; Trible, R. P., et al., 2006, Id.). Accordingly, binding of Nef to Hck, or derivative thereof, creates a unique active kinase conformation (Lerner, E. C. and Smithgall, T. E., 2002, *Nat. Struct. Biol.* 9:365-369; Lerner, E. C., Trible, R. P., Schiavone, A. P., Hochrein, J. M., Engen, J. R. and Smithgall, T. E., 2005, *J. Biol. Chem.* 280:40832-40837), which represents an attractive target for selective inhibitor discovery.

To identify inhibitors of the Nef:SFK (e.g., Nef:Hck) complex, using a cell-based assay was developed in which Nef:Hck (or derivative thereof) signaling drives a simple readable result (e.g., color change, cell density, and the like) amenable to high-throughput screening. As provided herein, the present assay contemplates yeast, where ectopic expression of active c-Src is well known to induce growth arrest (Brugge, J. S., Jurassic, G., Andersen, J., Queral-Lustig, A., Fedor-Chaiken, M. and Broach, J. R., 1987, *Mol. Cell Biol.* 7:2180-2187; Florio, M., Wilson, L. K., Trager, J. B., Thorner, J. and Martin, G. S., 1994, *Mol. Biol. Cell* 5:283-296; Kornbluth, S., Jove, R. and Hanafusa, H., 1987, *Proc. Natl. Acad. Sci. U.S.A.* 84:4455-4459; Murphy, S. M., Bergman, M. and Morgan, D. O., 1993, *Mol. Cell Biol.* 13:5290-5300). Co-expression of C-terminal Src kinase (Csk), a negative regulator of SFKs, reverses Src-mediated growth suppression in yeast by phosphorylating the c-Src negative regulatory tail and repressing kinase activity (Murphy, S. M., Bergman, M. and Morgan, D. O., 1993, *Mol. Cell Biol.* 13:5290-5300; Nada, S., Yagi, T., Takeda, H., Tokunaga, T., Nakagawa, H., Ikawa, Y., Okada, M. and Aizawa, S., 1993, *Cell* 73:1125-1135; Superti-Furga, G., Fumagalli, S., Koegl, M., Courtneidge, S. A. and Draetta, G., 1993, *EMBO J.* 12:2625-2634; Trible, R. P., et al., 2006, Id.). Indeed, using another yeast-based system, it has been shown that other members of the Src kinase family also induce yeast growth arrest in a Csk-reversible manner (Trible, R. P., et al., 2006, Id.), and co-expression of HIV-1 Nef selectively overcomes this negative regulation for Hck, Lyn, and c-Src, resulting in kinase re-activation and growth arrest. Accordingly, these observations suggested that the yeast system is suitable for an inhibitor screen, as compounds that block Nef-induced SFK signaling can rescue cell growth.

To simplify the yeast assay and facilitate the use thereof in high-throughput screening protocols, the Hck tail sequence was mutated to afford a high-affinity SH2-binding motif of Hck-YEEI (SEQ ID NO: 4). Without wishing to be bound by any theory, it is believed that this substitution redirects autophosphorylation from the activation loop to the tail, leading to intramolecular engagement of the SH2 domain and down-regulation of kinase activity in the absence of Csk (Schindler, T., Sicheri, F., Pico, A., Gazit, A., Levitzki, A. and Kuriyan, J., 1999, *Mol. Cell* 3:639-648). It is reported that the X-ray crystal structure of this modified form of Hck (Hck-YEEI) (SEQ ID NO: 4) is nearly identical to that of native Hck that has been down-regulated by Csk (Schindler, T., et al., Id.; Sicheri, F., Moarefi, I. and Kuriyan, J., 1997, *Nature* 385:602-609). To determine whether the YEEI (SEQ ID NO: 5) substitution was sufficient to downregulate Hck in yeast, wild-type Hck and Hck-YEEI (SEQ ID NO: 4) were expressed in the presence and absence of Csk. In these experiments, Hck-YEEI (SEQ ID NO: 4) failed to suppress yeast growth, and showed reduced kinase activity compared with wild-type Hck on anti-phosphotyrosine immunoblots of yeast cell lysates. Co-expression of Csk reduced wild-type Hck kinase activity and reversed growth suppression, but had no additional effect on Hck-YEEI (SEQ ID NO: 4) auto-downregulation. Accordingly, these results demonstrate that Hck-YEEI (SEQ ID NO: 4) effectively models the behavior of Csk-downregulated wild-type Hck in yeast. Thus, HIV-1 Nef activates Csk-downregulated Hck in yeast, leading to growth suppression (Trible, R. P., et al., 2006, Id.). To determine whether Nef similarly activates auto-inhibited Hck-YEEI (SEQ ID NO: 4), yeast were transformed with plasmids encoding wild-type Hck or Hck-YEEI (SEQ ID NO: 4) in the presence or absence of Csk and Nef. Csk and Nef expression had no effect on yeast growth in the absence of Hck. Wild-type Hck suppressed yeast growth, and this effect was reversed upon co-expression of Csk. Nef strongly enhanced Hck-mediated growth suppression independent of Csk as observed previously (Trible, R. P., et al., 2006, Id). Importantly, co-expression of Nef with Hck-YEEI (SEQ ID NO: 4) also induced a strong growth suppressive effect that was unaffected by Csk. Co-expression of Nef with wild-type Hck resulted in much stronger tyrosine phosphorylation of yeast proteins than observed with Hck alone or in the presence of Csk. Nef produced a similar increase in the kinase activity of Hck-YEEI (SEQ ID NO: 4). The effects of Nef on yeast protein-tyrosine phosphorylation by wild-type Hck and Hck-YEEI (SEQ ID NO: 4) were unaffected by Csk. In all cases, a strong inverse correlation was observed between Hck kinase activity and yeast growth. Thus, Nef strongly activates Hck-YEEI (SEQ ID NO: 4) and induces a growth-suppressive phenotype very similar to that observed with wild-type Hck.

Because Nef-induced activation of Hck-YEEI (SEQ ID NO: 4) causes growth arrest, inhibitors of this complex should restore growth, thus providing the basis for an inhibitor screen.

This principle was tested with A-419259, a potent inhibitor of Hck and other SFKs (Meyn, M. A., III, Schreiner, S. J., Dumitrescu, T. P., Nau, G. J. and Smithgall, T. E., 2005, *Mol. Pharmacol.* 68:1320-1330; Wilson, M. B., Schreiner, S. J., Choi, H. J., Kamens, J. and Smithgall, T. E., 2002, *Oncogene*, 21:8075-8088). Liquid cultures of yeast co-expressing Hck-YEEI (SEQ ID NO: 4), and Nef were grown in the presence or absence of A-419259, and growth was monitored as the change in optical density at 600 nm. A-419259 significantly reversed the growth suppression induced by the Nef:Hck-YEEI (SEQ ID NO: 4) complex at both 1 µM and 5 µM in comparison to untreated cultures. At 5 µM, A-419259 treatment was nearly as effective as mutation of the Nef PxxP motif essential for SH3 binding in terms of reversing the growth arrest. This effect of A-419259 correlated with a decrease in tyrosine phosphorylation of yeast proteins to control levels in the inhibitor-treated cultures. Thus, the ability of A-419259 to rescue growth induced by the Nef:Hck-YEEI (SEQ ID NO: 4) complex supported the broader use of the yeast-based system to identify selective inhibitors of Nef: SFK signaling.

Inhibitor Screening Based on Nef:SFK Kinase Activity in a Yeast Assay System

Yeast cultures expressing the Nef:Hck-YEEI (SEQ ID NO: 4) complex were used to screen a chemical library of 2496 discrete heterocyclic compounds (Example 5). In the first pass, each compound was tested in duplicate at 10 µM for its ability to increase growth of Nef:Hck-YEEI (SEQ ID NO: 4) cultures relative to controls incubated with the carrier solvent alone. From this primary screen, 170 compounds were observed to restore growth of Nef:Hck-YEEI (SEQ ID NO: 4) cultures by at least 10% over untreated controls. These compounds were then re-screened at 10 µM in comparison to 5 µM A-419259, the control SFK inhibitor. Of these, fifteen compounds were observed to rescue growth to at least 25% of the values observed with A-419259-treated positive controls. Each of these compounds was then tested a third time over a range of concentrations to verify growth recovery of Nef: Hck-YEEI (SEQ ID NO: 4) cultures compared with A-419259.

Lead compounds from the yeast screen were evaluated for activity in a Nef-dependent HIV replication assay. For these experiments, U87MG astroglioma cells engineered to express the HIV-1 co-receptors CD4 and CXCR4 were employed. Replication of HIV-1 NL4-3 is dependent upon an intact viral nef gene in these cells, making this system suitable to evaluate leads from the Nef-directed screen. U87MG cells were infected with HIV-1 in the presence of the top five compounds identified in the yeast screen, and HIV replication was monitored as p24 release into the culture supernatant 4 days later, as known in the art. As known in the art, "p24" refers to a constituent protein of the capsid of HIV-1. As judged by the results of this experiment, Compounds Ia and IIa significantly suppressed HIV replication in this assay (FIG. 1). Neither of these compounds was cytotoxic to U87MG cells up to 50 µM, as judged by Alamar Blue (resazurin) cell viability assay as known in the art, indicating that the inhibition of HIV replication is not due to non-specific effects on cell growth. Subsequent concentration-response studies revealed that Compound Ia, a benzenesulfonamide derivative of 2,3-diamino quinoxaline, blocked HIV replication with an $IC_{50}$ (i.e., concentration resulting in 50% inhibition) value of approximately 130 nM in this system.

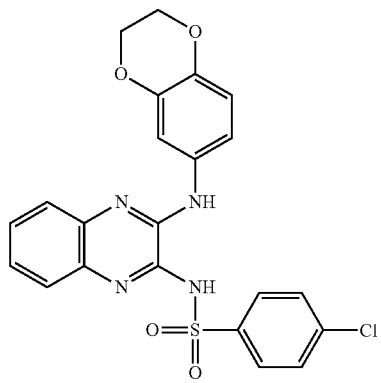

Ia

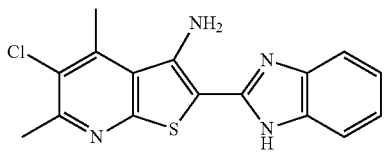

IIa

To explore whether other 2,3-diaminoquinoxaline derivatives display anti-HIV effects, 20 analogs of Compound Ia (Compounds Q1-Q20 having structures indicated herein) were compared with respect to anti-HIV activity. See Table 1. Compounds Q1-Q20 were evaluated in the U87MG cell system, supra, at 5 μM, with release of p24 determined by standard technique (ELISA) after 4 days. The data of Table 1 are presented as percent p24 release relative to control in the absence of compound. Cytotoxicity data were obtained for Compounds Q1-Q20 in U87MG cells incubated with each compound at 30 μM using the CellTiter blue assay (Promega, Madison Wis.) at 96 hr incubation, following manufacturer's recommended procedures. Data are expressed as percent viable cells relative to untreated control culture.

TABLE 1

Inhibition of HIV-1 replication and cytotoxicity for Compounds Q1-Q20 in U87MG cells.

| Compound | HIV p24% Control @ day 4 | Cytotoxicity, Viable cell % control |
| --- | --- | --- |
| Q1 | 4 | 98 |
| Q2* | 10 | 100 |

TABLE 1-continued
Inhibition of HIV-1 replication and cytotoxicity for
Compounds Q1-Q20 in U87MG cells.
| Compound | HIV p24% Control @ day 4 | Cytotoxicity, Viable cell % control |
|---|---|---|
| 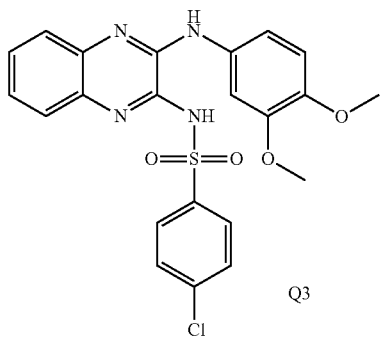 Q3 | 13 | 100 |
| 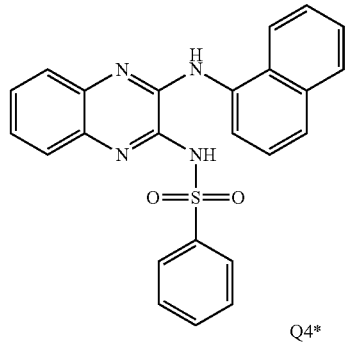 Q4* | 26 | 100 |
| 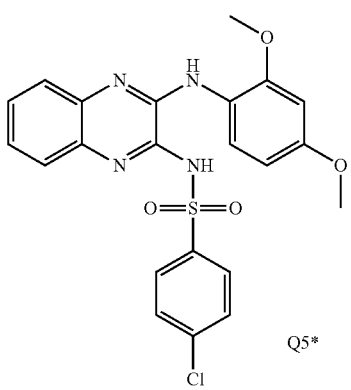 Q5* | 26 | 96 |
| 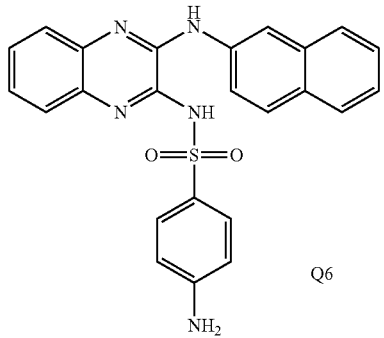 Q6 | 40 | 92 |

TABLE 1-continued

Inhibition of HIV-1 replication and cytotoxicity for
Compounds Q1-Q20 in U87MG cells.

| Compound | HIV p24% Control @ day 4 | Cytotoxicity, Viable cell % control |
| --- | --- | --- |
| Q7 | 42 | 97 |
| Q8 | 55 | 90 |
| Q9 | 60 | 100 |
| Q10 | 62 | 95 |

TABLE 1-continued
Inhibition of HIV-1 replication and cytotoxicity for Compounds Q1-Q20 in U87MG cells.
| Compound | HIV p24% Control @ day 4 | Cytotoxicity, Viable cell % control |
|---|---|---|
| 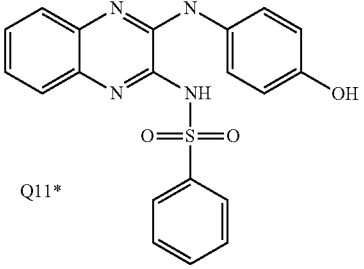 Q11* | 68 | 88 |
| 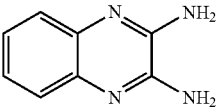 Q12 | 74 | 90 |
| 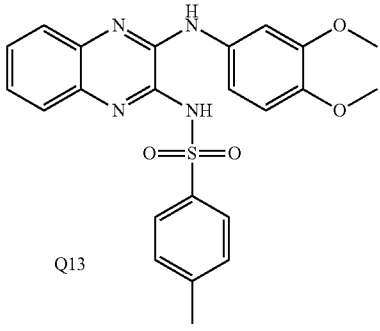 Q13 | 82 | 91 |
| 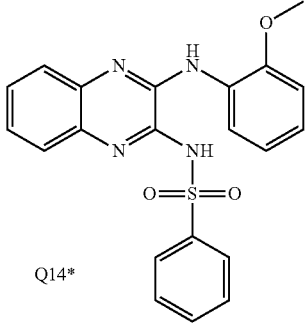 Q14* | 87 | 93 |
| 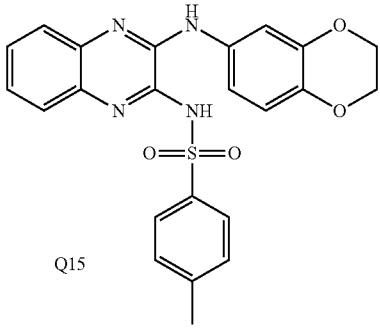 Q15 | 88 | 96 |

TABLE 1-continued
Inhibition of HIV-1 replication and cytotoxicity for Compounds Q1-Q20 in U87MG cells.
| Compound | HIV p24% Control @ day 4 | Cytotoxicity, Viable cell % control |
|---|---|---|
| 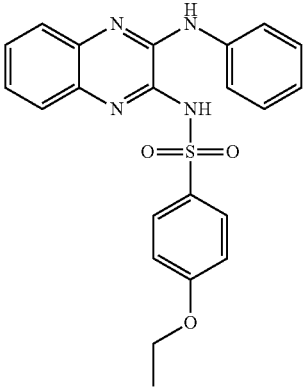 Q16 | 91 | 100 |
| 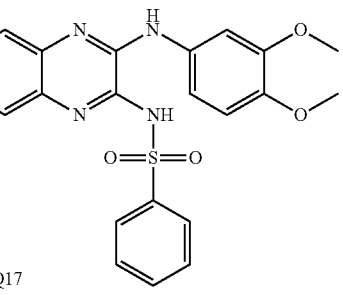 Q17 | 100 | 97 |
| 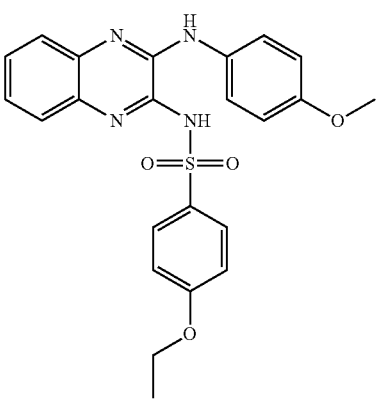 Q18 | 112 | 99 |
| 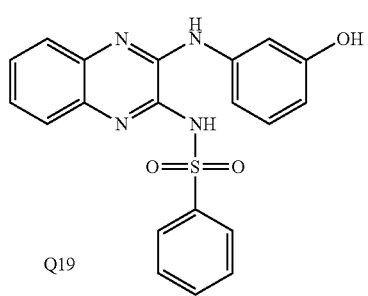 Q19 | 114 | 92 |

TABLE 1-continued

Inhibition of HIV-1 replication and cytotoxicity for Compounds Q1-Q20 in U87MG cells.

| Compound | HIV p24% Control @ day 4 | Cytotoxicity, Viable cell % control |
|---|---|---|
| 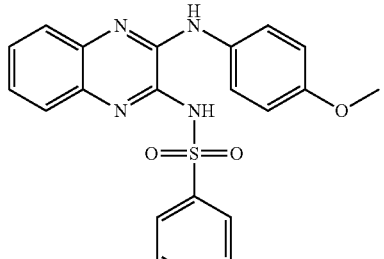 Q20 | 119 | 89 |

*Partial loss of solubility observed under incubation and/or assay conditions

Compounds Q1-Q20 display a remarkable range of anti-HIV effects. The unsubstituted 2,3-diaminoquinoxaline Compound Q12 showed weak activity, suggesting an important role for the benzenesulfonamide and dihydrobenzodioxine substituents. A variety of substitutions were tolerated in place of the dihydrobenzodioxine, with various phenyl, methoxyphenyl, and naphthyl derivatives exhibiting the strongest activity. p-chloro substitution of the benzenesulfonamide also appears to be critical, as removal of the halogen converted one of the most active compounds, Compound Q3, to one of the least active, Compound Q17. Based on the structure-activity analysis of the 2,3-diamino quinoxaline derivatives shown in Table 1, the present inventors propose that quinoxaline compounds of the present invention that have a bulky hydrophobic substituents at $Cy^1$ and a p-chloro substitution on the benzenesulfonamide ring should display enhanced anti-HIV activity.

To explore this prospect, the inventors synthesized and tested two 2,3-diamino quinoxaline derivatives Q21 and Q22 which differ from each other in their position of attachment to the naphthyl ring.

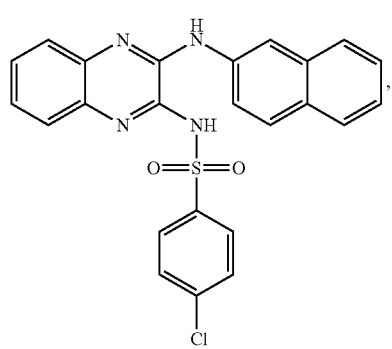
Q21

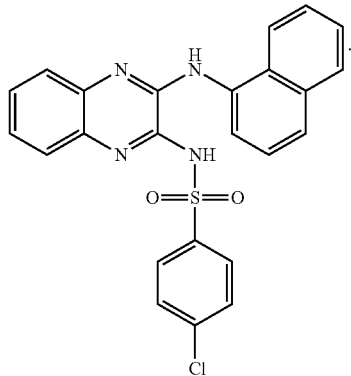
Q22

Figure 2:
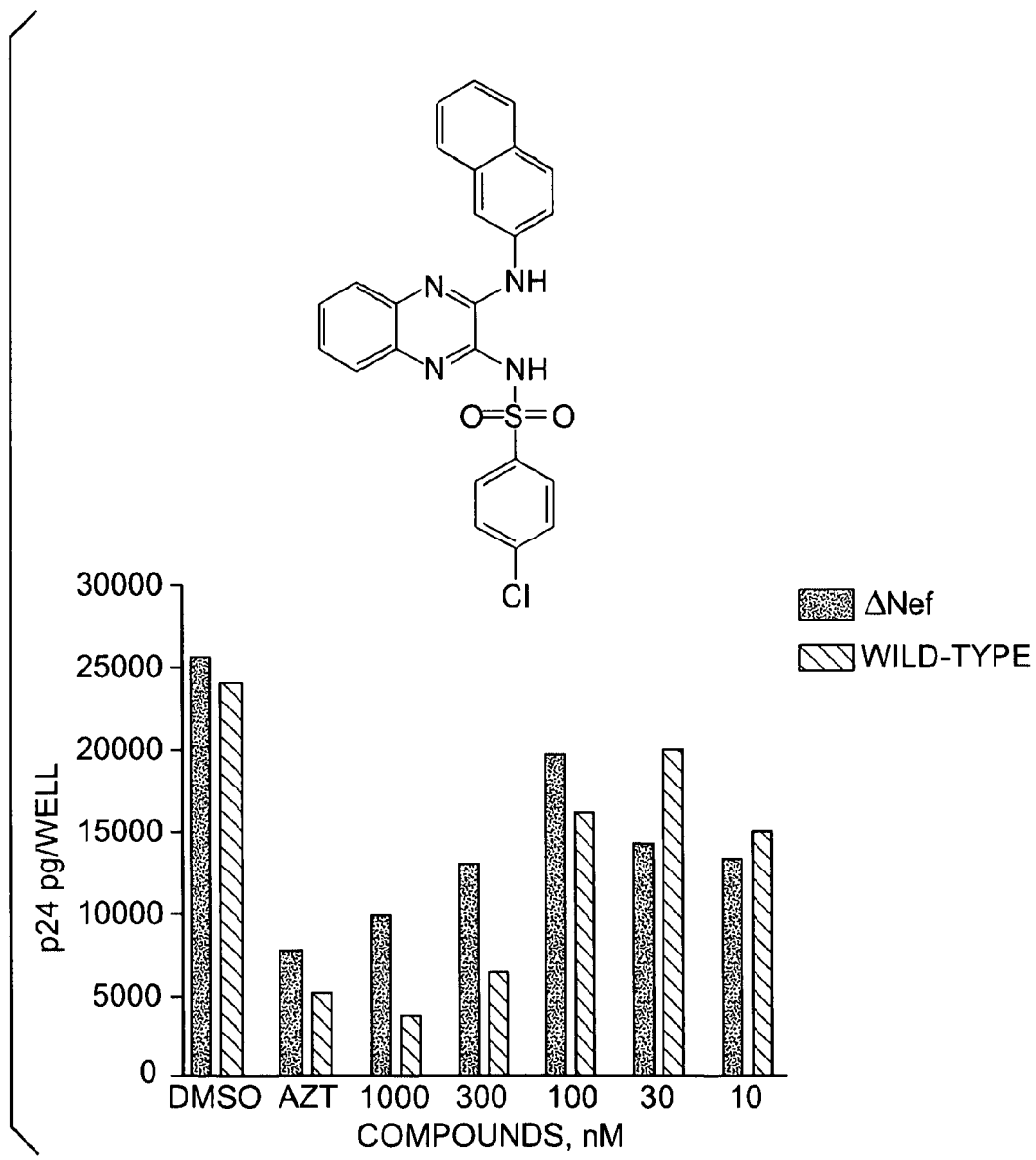
FIG. 2: Inhibition of replication of pseudotyped NL43 HIV-1 by 4-chloro-N-(3-naphthalen-2-ylamino)benzenesulfonamide.
Figure 3:
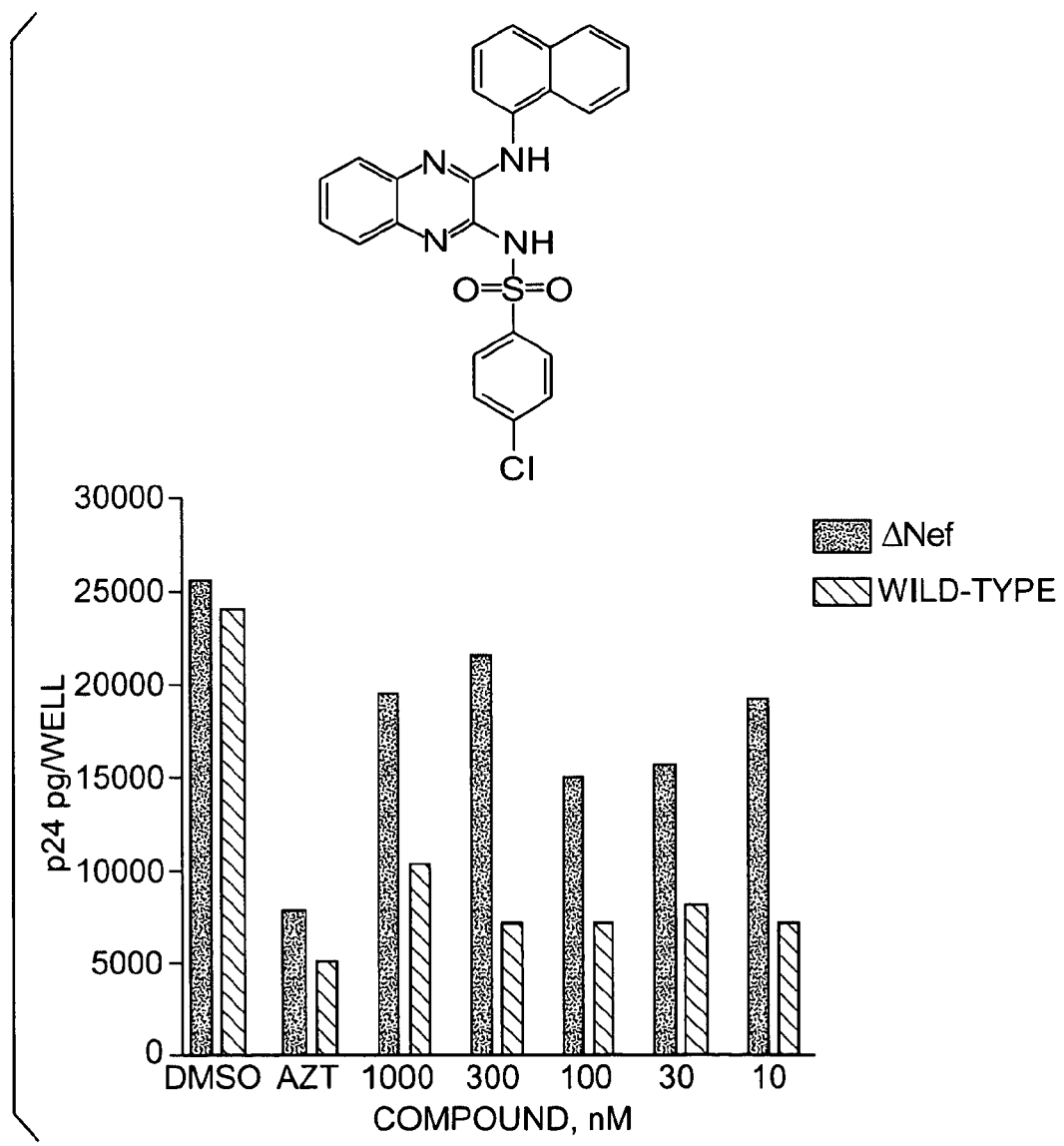
FIG. 3: Inhibition of replication of pseudotyped NL43 HIV-1 by 4-chloro-N-(3-naphthalen-1-ylamino)benzenesulfonamide.

Thus, in Q21 the naphthyl ring is attached to the 2,3-diamino quinoxaline scaffold at carbon-2 (C-2), while in compound Q22 the naphthyl group is attached through carbon-1 (C-1). Both quinoxaline derivatives were tested for their ability to inhibit pseudotyped NL43 HIV-1 replication ex vivo (FIGS. 2 and 3). Derivative Q2 was used as the control in this experiment. FIGS. 1-3, display the results for viral inhibition by Q21 and Q22 in U87MG cells infected with wild-type NL43 HIV-1 and a Nef-deficient NL43 HIV-1 virus. Both quinoxaline derivatives, Q21 and Q22, are potent inhibitors of viral infection as is the standard compound Q2. Unlike Q2 and Q21, however, derivative Q22 is selective and more potent at inhibiting the replication of wild-type virus, when compared to Nef-deficient virus. As shown in FIG. 3, Q22 shows Nef-dependent inhibition for wild-type viral replication throughout the concentration range tested. Because Nef plays a crucial role in HIV-1 replication, 2,3-diamino quinoxaline derivatives such as Q22 are valuable pharmaceutical tools for identifying HIV-1 inhibitors.

Table 1 also shows that none of the exemplified quinoxaline derivatives displays significant cytotoxicity against U87MG cells. This further substantiates 2,3-diamino quinoxaline as a candidate scaffold for anti-HIV drug purposes.

In Vitro Assay for Nef:SFK Kinase Activity

In certain embodiments of the inventive method of screening for an inhibitor of kinase activity of a Nef:SFK complex, the Nef:SFK assay system is an in vitro assay system that comprises Nef or mutant thereof, an SFK or mutant thereof, ATP, and a substrate suitable for detection of kinase activity, and the determination of kinase activity includes detecting phosphorylation of the substrate, wherein inhibition of phosphorylation indicates inhibition of kinase activity. In some embodiments, the Nef:SFK complex is a Nef:Hck complex, wherein the Nef:Hck complex includes Nef or mutant thereof and Hck or mutant thereof. In some embodiments, the Nef: Hck complex includes Nef or mutant thereof and Hck-YEEI (SEQ ID NO: 4) or mutant thereof. In some embodiments, the Nef: Hck complex includes Nef and Hck-YEEI (SEQ ID NO: 4). In some embodiments, the Nef:Hck complex consists of Nef and Hck-YEEI (SEQ ID NO: 4).

Figure 4:
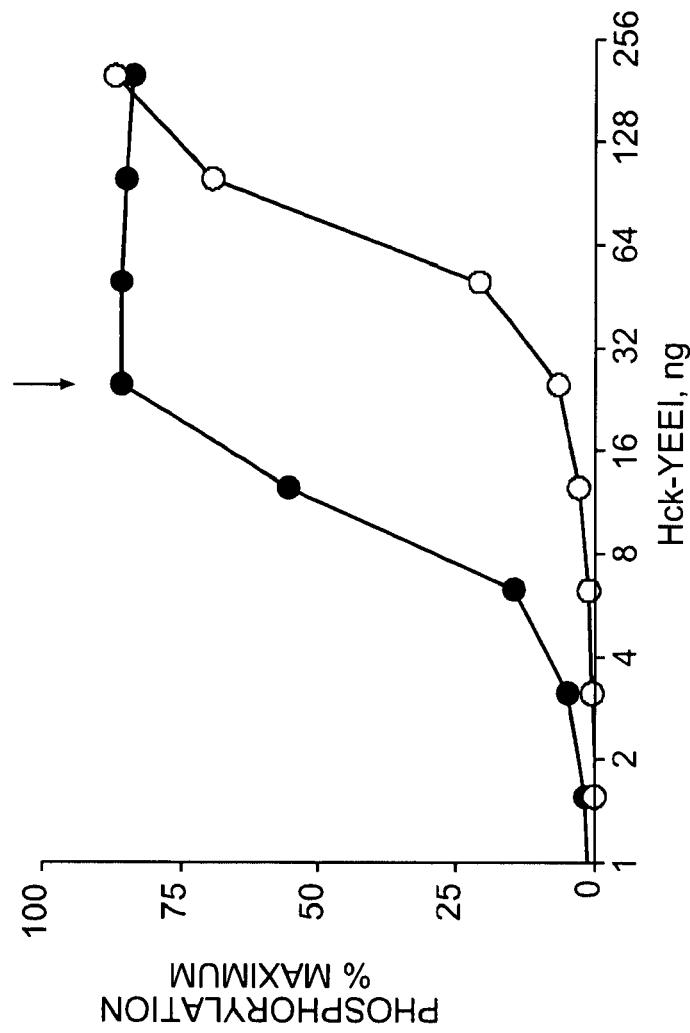
FIG. 4: Screening for Nef:Hck inhibitors from a chemical library using a Hck surrogate, Hck-YEEI (SEQ ID NO: 4) under conditions where Hck-YEEI (SEQ ID NO: 4) activation is dependent upon Nef (arrow). The extent of phosphorylation is expressed as mean percent of phosphorylation relative to a control phosphopeptide ±S.D.

As described herein, assay conditions were developed under which Hck-YEEI (SEQ ID NO: 4) activation was dependent upon the presence of Nef. Accordingly, recombinant Hck was purified from Sf9 insect cells in the downregulated Hck-YEEI (SEQ ID NO: 4) form and assayed with a peptide substrate and ATP as described (Example 2). Reactions were run in the presence of increasing amounts of Hck-YEEI (SEQ ID NO: 4) alone (open circles), and the extent of peptide substrate phosphorylation was observed to increase as a function of the amount of Hck-YEEI (SEQ ID NO: 4) added to the assay, (FIG. 4A). This experiment was repeated in the presence of a 10-fold molar excess of HIV-1 Nef (closed circles), at each Hck-YEEI (SEQ ID NO: 4) concentration. The presence of Nef markedly shifted the Hck-YEEI (SEQ ID NO: 4) activation curve to the left, indicative of its ability to bind to Hck and relieve the inhibitory effect of the SH3 domain on kinase activity as reported (Moarefi, I. et al., 1997, *Nature* 385:650-653). The arrow in FIG. 4, indicates the Hck-YEEI (SEQ ID NO: 4) concentration at which Hck activation is dependent on the presence of Nef and serves as a reference point for screening chemical libraries of potential inhibitors of the Nef-Hck complex.

Inhibitor Screening Based on Nef:SFK Kinase Activity in a In Vitro Assay System

The Nef:Hck-YEEI (SEQ ID NO: 4) complex described herein was used to screen chemical libraries consisting of approximately 10,000 discrete compounds for inhibitory activity. The libraries were populated with structures biased towards kinase and phosphatase inhibitors as well as more diverse structures. The primary screen yielded four distinct scaffolds represented as Formulae II-V.

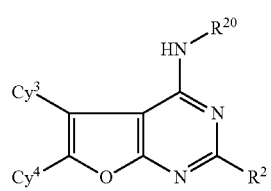

II

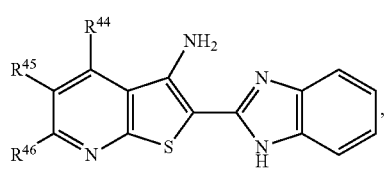

III

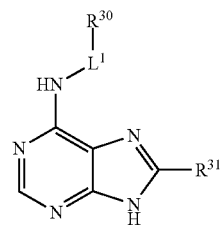

IV

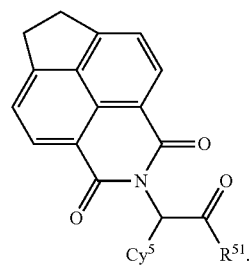

V

All of the compounds were initially screened in duplicate at 10 μM. The term "hit" refers to a compound which under test conditions as described herein provides at least 50% inhibition relative to untreated controls. Of the four hits identified in the primary screen, the efficacy of three hits to inhibit Nef:SFK kinase activity was confirmed in subsequent dose-response assays. All of the confirmed hits were obtained from the kinase inhibitor-biased library. The structures of the three most potent compounds (Formulae IIIa, IVa, and Va) are shown below:

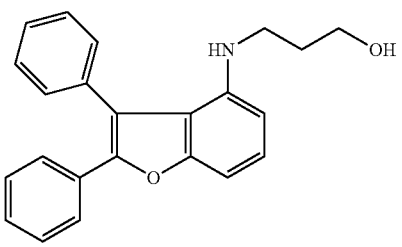

IIIa

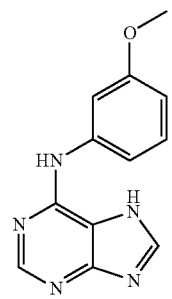

IVa

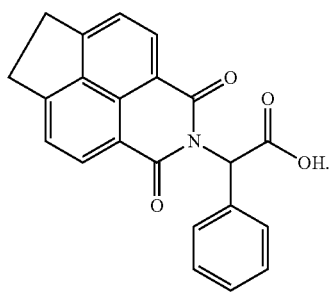

Va

The strongest inhibitors of the Nef:Hck complex identified in the library screen were then evaluated for anti-HIV activity. It is understood that "strongest" and like terms in the context of inhibitors identified in a library screen refer to compounds that inhibit at the lowest concentrations. For these experiments, the U87MG astroglioma cell line was used as a model system. HIV-1 replication is dependent upon Nef in these cells, (FIG. 5A), and Nef expression stimulates endogenous SFK autophosphorylation in these cells (not shown), providing a system to evaluate the impact of the compounds on Nef-dependent HIV replication. U87MG cells were infected with HIV-1 strain NL4-3 as well as an isogenic variant that fails to express Nef (ΔNef), over a wide range of viral titers and in the presence of each compound at 5 µM. Viral replication was assessed as HIV p24 antigen release into the culture supernatant 4 and/or 5 days later. Methods for the assay of p24 in culture supernatant are well known in the art and include, for example without limitation, immunochemical methods. As shown in FIGS. 6A and 6B, each of these compounds displayed anti-HIV activity, with compound of Formula IIIa (Table 2) suppressing HIV replication to undetectable levels, which is remarkable.

Because of demonstrated strong anti-HIV activity, Compound IIIa was studied in more detail. This compound, 3-(5,6-diphenylfuro[2,3-d]pyrimidin-4-ylamino)propan-1-01 (DFP-4AP), has not been previously reported as a protein kinase inhibitor. A dose response study against the Nef:Hck-YEEI (SEQ ID NO: 4) complex revealed that DFP-4AP blocked kinase activity with an $IC_{50}$ of about 3 (FIG. 5B). The term "about" in the context of a numeric value refers to the numeric value +/−10% thereof. The anti-HIV activity of DFP-4AP was determined by titration in the U87MG system, which revealed that DFP-4AP blocked HIV replication with an $IC_{50}$ value of about 6 µM (FIG. 5C).

To determine whether diphenylfuropyrimidines more generally display anti-HIV activity, structural analogs contemplated by the present invention were compared with respect to anti-HIV activity relative to that of DFP-4AP in U87MG cells. See Table 2, which discloses the effect of furopyrimidines in HIV replication assay using the Nef-dependent U87MG cell system described herein. Incubation and assay conditions for p24, and for cytotoxicity measurements, were as described for Table 1.

TABLE 2

Inhibition of HIV-1 replication and cytotoxicity for furopyrimidines.

| Cmpd. | Structure | HIV p24% Control @ day 4 | Cytotoxicity, Viable cell % control |
|---|---|---|---|
| IIIa | 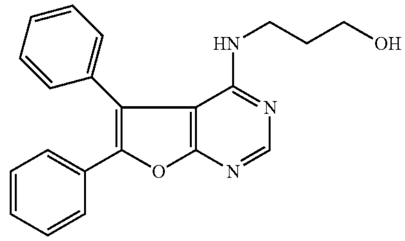 [SMILES: OCCCNc1ncnc2oc(-c3ccccc3)c(-c3ccccc3)c12] | 20 | 95 |
| IIIb | 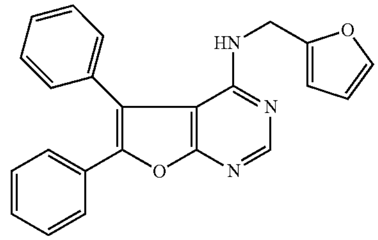 [SMILES: c1ccc(-c2oc3ncnc(NCc4ccco4)c3c2-c2ccccc2)cc1] | 8 | 109 |
| IIIc | 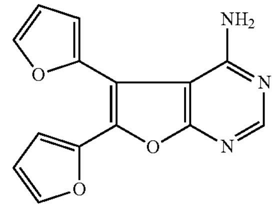 [SMILES: Nc1ncnc2oc(-c3ccco3)c(-c3ccco3)c12] | 20 | N/A |

TABLE 2-continued

Inhibition of HIV-1 replication and cytotoxicity for furopyrimidines.

| Cmpd. | Structure | HIV p24% Control @ day 4 | Cytotoxicity, Viable cell % control |
|---|---|---|---|
| IIId | 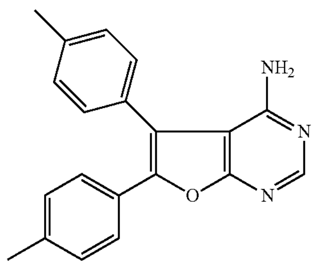 [SMILES: Cc1ccc(-c2oc3ncnc(N)c3c2-c2ccc(C)cc2)cc1] | 29 | 90 |
| IIIe | 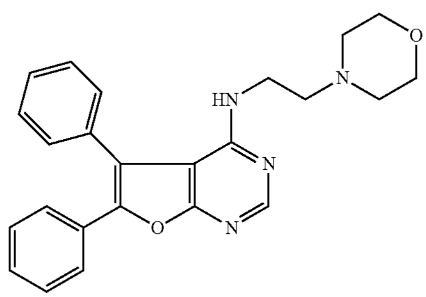 [SMILES: c1ccc(-c2oc3ncnc(NCCN4CCOCC4)c3c2-c2ccccc2)cc1] | 39 | 89 |
| IIIf | 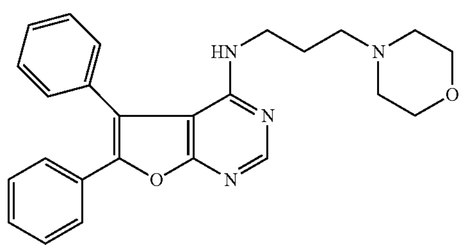 [SMILES: c1ccc(-c2oc3ncnc(NCCCN4CCOCC4)c3c2-c2ccccc2)cc1] | 47 | 99 |
| IIIg | 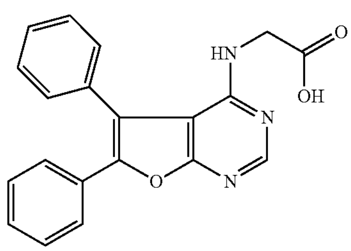 [SMILES: O=C(O)CNc1ncnc2oc(-c3ccccc3)c(-c3ccccc3)c12] | 58 | 100 |

TABLE 2-continued

Inhibition of HIV-1 replication and cytotoxicity for furopyrimidines.

| Cmpd. | Structure | HIV p24% Control @ day 4 | Cytotoxicity, Viable cell % control |
|---|---|---|---|
| IIIh | 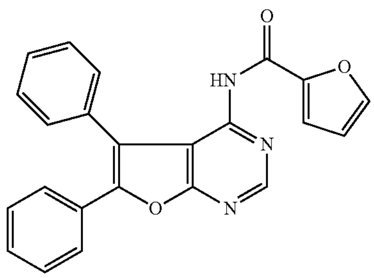 [SMILES: O=C(Nc1ncnc2oc(-c3ccccc3)c(-c3ccccc3)c12)c1ccco1] | 59 | 89 |
| IIIi | 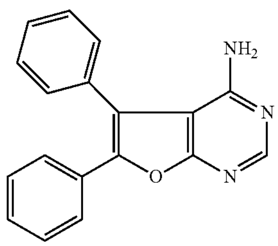 [SMILES: Nc1ncnc2oc(-c3ccccc3)c(-c3ccccc3)c12] | 72 | 94 |
| IIIj | 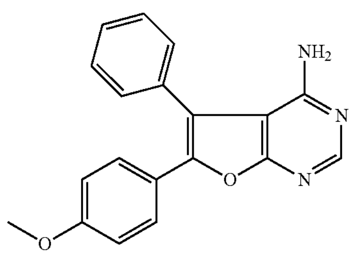 [SMILES: COc1ccc(-c2oc3ncnc(N)c3c2-c2ccccc2)cc1] | 73 | 97 |
| IIIk | 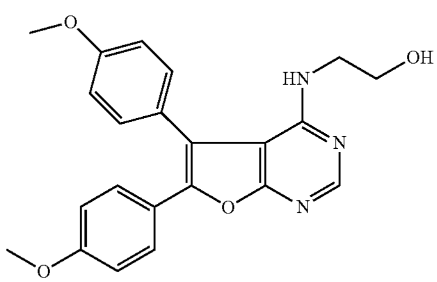 [SMILES: COc1ccc(-c2oc3ncnc(NCCO)c3c2-c2ccc(OC)cc2)cc1] | 76 | 88 |
| IIIL | 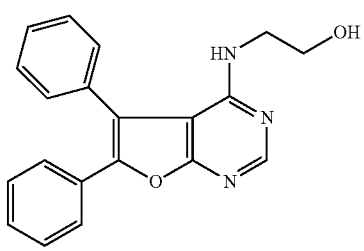 [SMILES: OCCNc1ncnc2oc(-c3ccccc3)c(-c3ccccc3)c12] | 93 | 94 |

The results shown in Table 2 reveal a range of anti-viral activities and identify the substituent present on the 4-amino group as a critical determinant of activity. For example, replacement of the original propanol substituent in DFP-4AP with a methyl-furanyl group enhanced anti-HIV activity further, while elimination of this substituent or simply shortening it by a single carbon substantially reduced anti-HIV activity. Importantly, neither DFP-4AP nor any of the other diphenylfuropyrimidine analogs displayed significant cytotoxicity in U87MG cells.

To investigate whether the presence of Nef affected the inhibitory action of diphenylfuropyrimidines against Hck in vitro, DFP-4AP (IIIa) and two of its analogs (i) DFP-4AB (IIIm), which has a slightly longer 4-aminobutanol side chain, and (ii) DFP-4PF (IIIq), with a bulkier 4-aminopropylfuran substituent (Scheme 1) were used. Each compound was tested in dose-response experiments for their ability to inhibit the Nef:Hck complex as well as Hck alone using the Z'-Lyte assay.

FIGS. 7A-7C display the percent inhibition of kinase activity for the exemplary compounds. For example, compound IIIa shows a modest but reproducible 2-fold increase in potency in the presence of Nef. This effect is more pronounced with the 4-aminobutanol analog (IIIm). Compound IIIm shows less activity for Hck while having a similar binding affinity for the Nef-Hck complex (FIG. 7B). Increasing the bulkiness of the amino substituent to a furan ring (IIIq) enhanced both potency and efficacy for the Nef:Hck complex vs. Hck alone (FIG. 7C). In this context, "potency" is a measure of drug activity expressed in terms of the amount required to produce an effect of given intensity. A highly potent drug evokes a larger response at low concentrations. Furthermore, the unsubstituted analog (IIIi) was virtually inactive against either Hck or the Nef:Hck complex, indicating that a substituent at the 4-amino position is important for activity and specificity of these compounds (data not shown).

Taken together, these results provide insights about binding interactions between diphenylfuropyrimidine compounds and Hck. For example, the greater potency of the furopyrimidines with the Nef:Hck complex suggest that the binding of Nef to Hck causes a change in the three dimensional structure of Hck that promotes its interaction with the furopyrimidine derivatives. Support for such a binding model comes from the X-ray crystal structure of the Lck kinase domain bound to a related diphenylfuropyrimidine-based inhibitor. See Dimauro, et al. (2007) *Bioorg. Med. Chem. Lett.*, V. 17, p2305-2309.

Based on the X-ray structure for the Lck-furopyrimidine analog, the inventors propose that the furopyrimidine moiety of compound IIIa (or other active furopyrimidine analogs), occupies the ATP-binding site of Hck. Engagement of SFK SH3 domains by Nef may influence the conformation of the active site in favor of compound binding. Indeed, experiments with mutants of Hck that fail to engage Nef show no difference in inhibitor sensitivity in the presence or absence of Nef (data not shown).

Figure 8A:
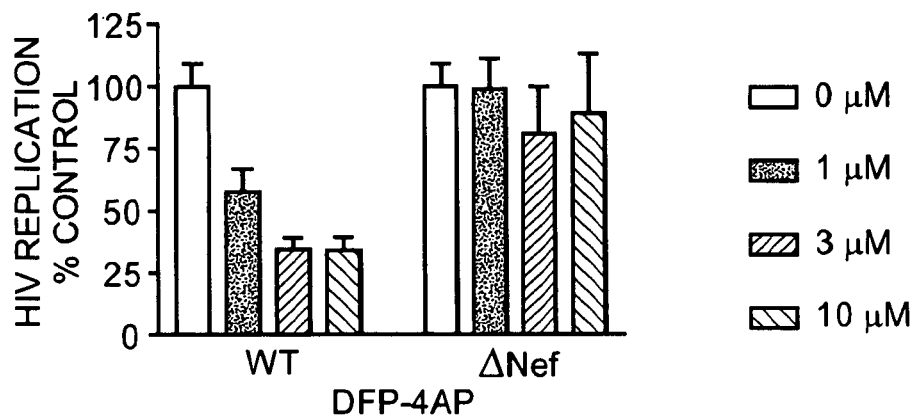
FIG. 8: Inhibition of wild-type and Nef deficient HIV-1 replication by diphenylfuropyrimidines. U87MG cells were infected with equal titers of wild-type HIV strain NL4-3 (WT) or a mutant that fails to express Nef (ΔNef) in the presence DFP-4AP, DFP-4AB, and DFP-4APF over a range of concentrations as shown. HIV p24 release was determined by ELISA at day 5 following the addition of the DFP-analogs. Data are presented as percent of p24 release observed in the absence of compound. U87MG cells were infected a viral density of 500 pg/ml. p24 as determined by ELISA.
Figure 8B:
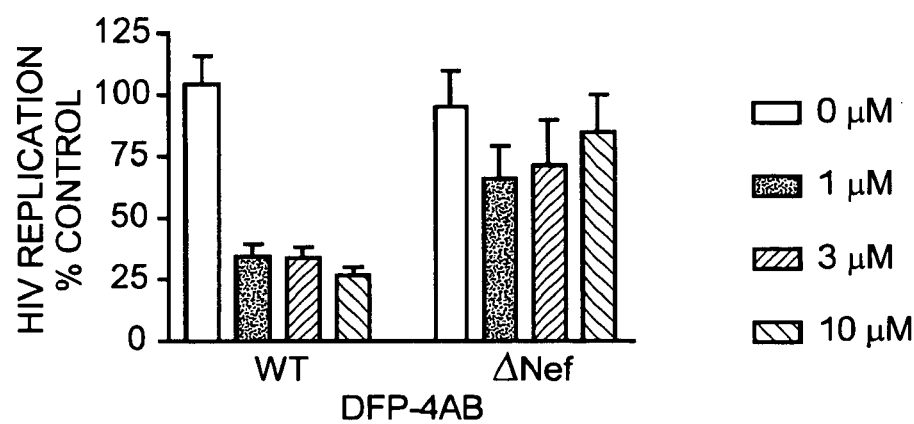
Figure 8C:
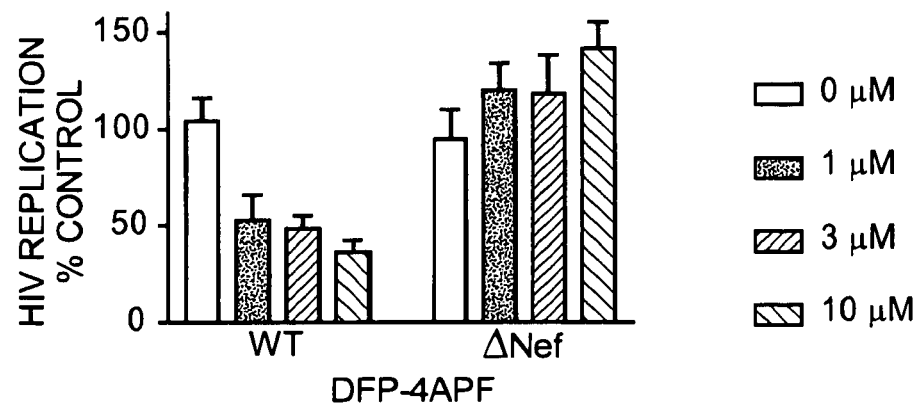

To address whether Nef is required for the anti-retroviral effects of these compounds, HIV replication assays in U87MG cells infected with either wild-type or Nef-defective HIV were carried out. As shown in FIGS. 5B and 8A, compound IIIa, blocked wild-type HIV replication with an $IC_{50}$ value in the low µM range. In contrast, IIIa had no effect on replication of the HIV-ΔNef mutant, even at 10 µM. Similar experiments with the other furopyrimidine analogs show that compounds IIIm and IIIq, selective for the Nef:Hck complex are potent inhibitors of wild-type HIV replication, with $IC_{50}$ values of 1 µM or less. See FIGS. 8B and 8C. Neither IIIm nor IIIq shows inhibition of HIV-ΔNef replication (FIGS. 8B and 8C, respectively), however.

These data indicate that 4-amino substituted DFP analogs block HIV replication through a Nef-dependent mechanism. To underscore the importance of substitution at the 4-amino group of pyrimidine, anti-retroviral activity was determined for IIIi (unsubstituted 4-amino group). This compound exhibited very weak anti-retroviral activity (data not shown). Yet, none of the exemplary compounds displayed cytotoxic effects to U87MG cells at concentrations up to 30 µM, determined using the resazurin reduction assay (data not shown).

Lead Compounds from Nef:SFK Kinase Activity in a Yeast Assay System

For compounds of Formula I, in accordance with the invention, $Cy^1$ is optionally substituted 1-naphthyl group. Illustrative substituents include a hydroxyl group, a halogen, a sulfate $(S(O)_3H)$ group, and/or a nitro group.

For example, the category of hydroxylated $Cy^1$ is illustrated groups that have the following structures:

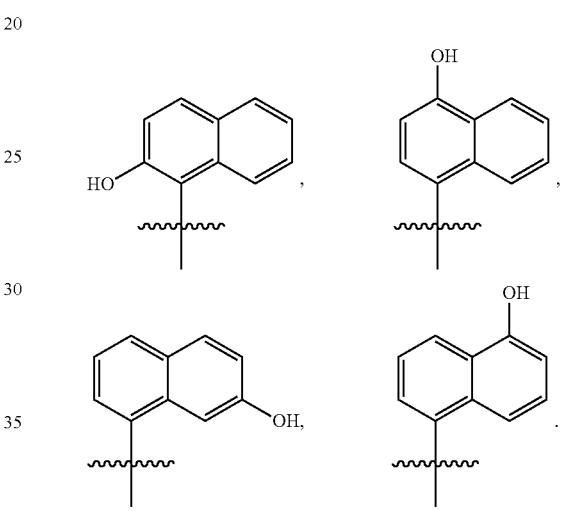

In certain embodiments, $Cy^1$ has multiple substituents. One or more of the substituents can be modified by the addition of one or more other groups. Exemplary of $C^1$ substituents are halogenated $Cy^1$ groups whose structures are shown below:

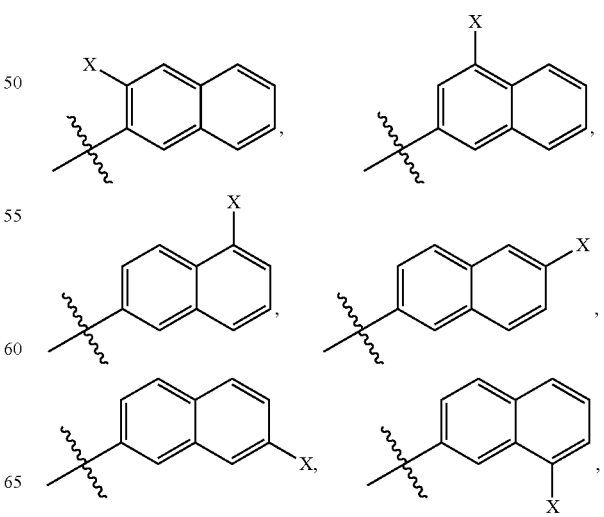

35

-continued

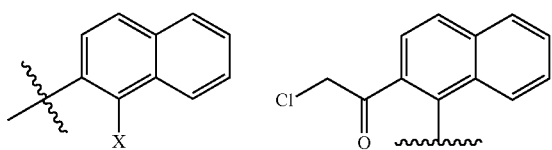

36

-continued

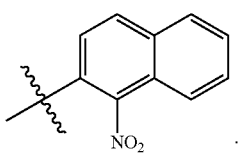

Also within the category of substituted Cy$^1$ are positional isomers of sulfated naphthyl groups, exemplified by the following structures:

Also contemplated within the category of Cy$^1$ substituents are relatively bulky hydrophobic groups shown below:

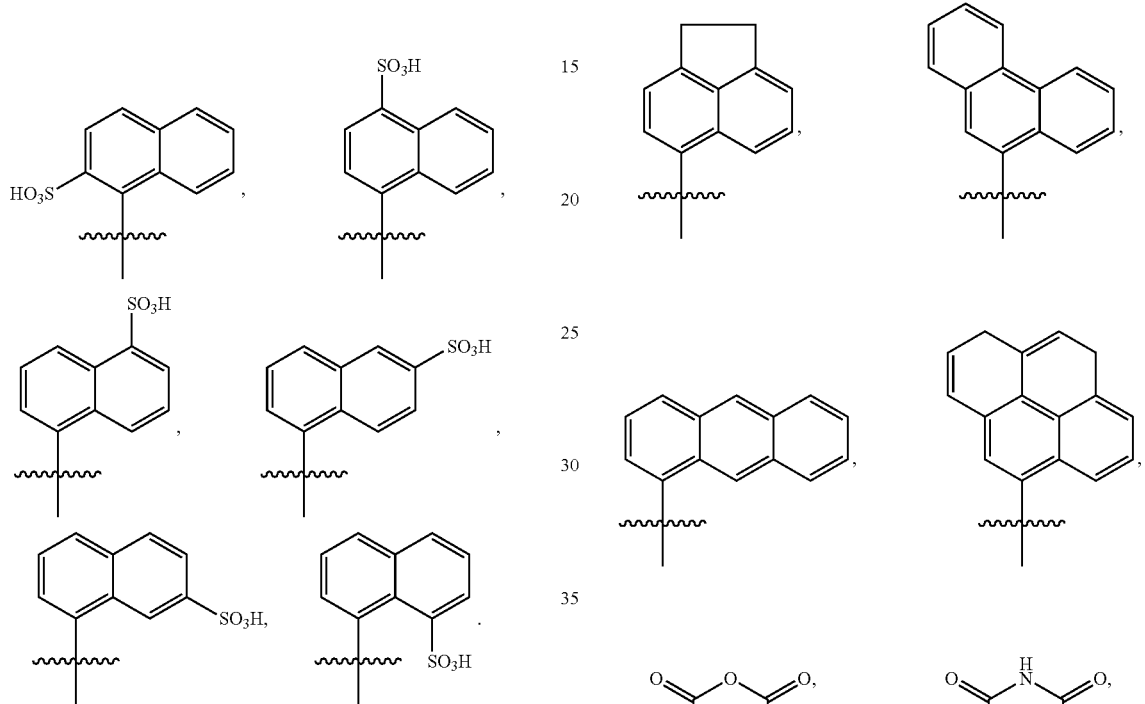

The naphthyl ring Cy$^1$ can be further substituted by a nitro group. Representative of nitrated derivates are the following:

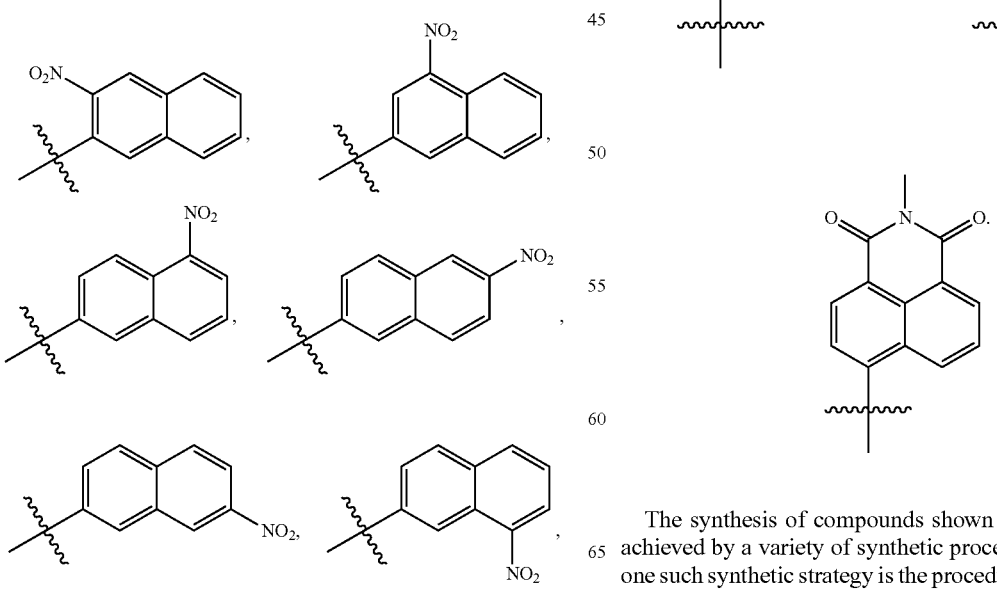

The synthesis of compounds shown in Formula I can be achieved by a variety of synthetic procedures. Illustrative of one such synthetic strategy is the procedure shown in Scheme 1.

Scheme 1
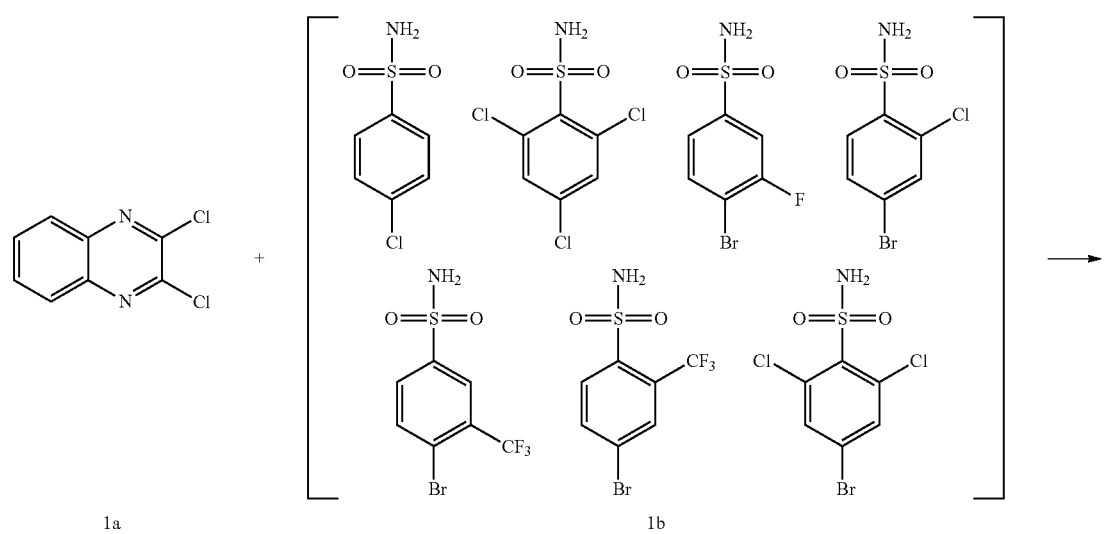
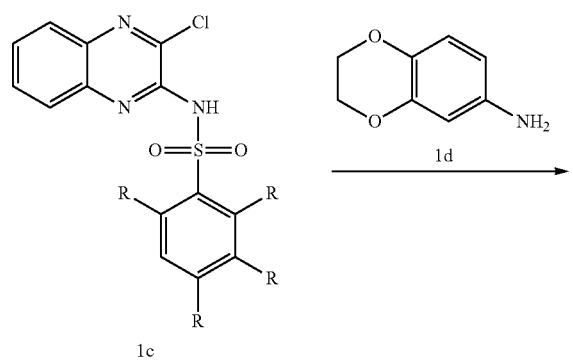
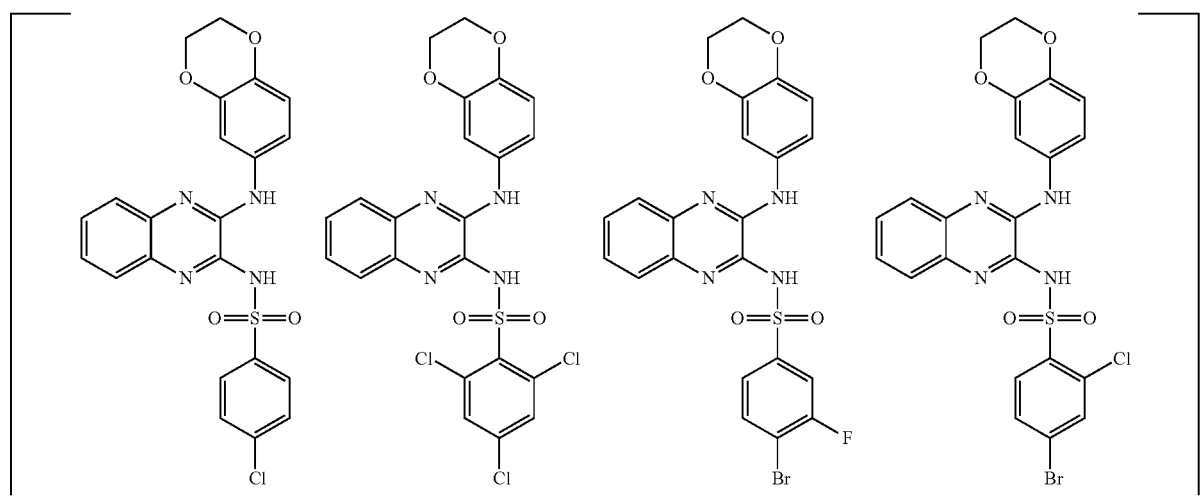

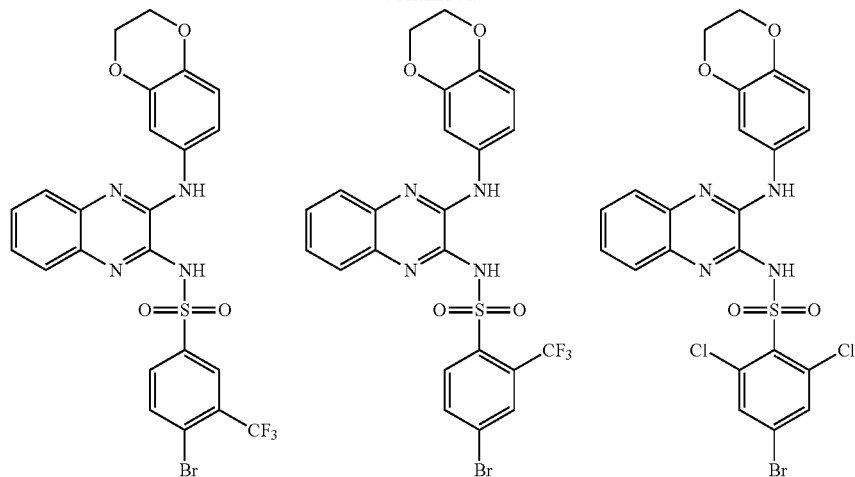

1e

With reference to Scheme 1, dichloroquinoxaline (Compound 1a) can react with a variety of optionally substituted aryl sulfonylamides (Compounds 1b) to afford the corresponding chloroquinoxalinyl arylsulfonylamides, Compounds 1c, wherein the substituent "R" refers to specific substitution as exemplified, but not limited to, substituents shown for Compound 1b. Suitable synthetic scheme for this reaction are well known in the art, including the Wolf reaction (Wolf, F. J., et al., 1949, *J. Am. Chem. Soc.* 71:6). Accordingly, reaction of compounds with structure of Compound 1c with, for example, an arylamine (e.g., Compound 1d), affords compounds of Formula I, as exemplified in Scheme 1 (e.g., Compounds 1e).

The synthetic strategy depicted above allows for the facile incorporation of nucleophilic amines at $Cy^1$. However, less nucleophilic amines such as naphthyl amines, are not incorporated into the quinoxaline scaffold by the synthetic route shown in Scheme 1. To facilitate reactions involving less nucleophilic amines, a palladium catalyzed cross-amination reaction was developed (Scheme 2). Thus, the cross-coupling of 1-naphthylamine with 2,3-dichloroquinoxaline in the presence of a base, ligand and palladium acetate catalyst under reflux conditions, allowed the facile introduction of the amine to give 3-chloro-(N-naphthylen-1-yl)-2-aminoquinoxaline (Compound 2c, Scheme 2).

Scheme 2:

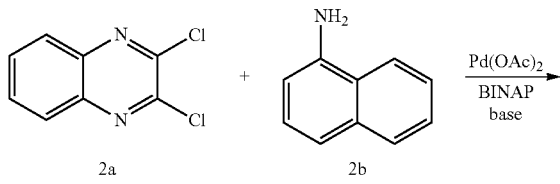

-continued

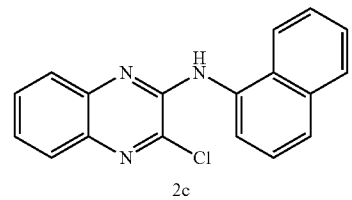

2c

To optimize the synthesis of Compound 2c, several small-scale reactions were carried out to determine the effect of solvent, base, catalyst load, and temperature on product formation. Table 3 enumerates the different synthetic variables in this regard, for each reaction.

As shown in Table 3, increasing the mole percent of palladium catalyst (entry 4), or adding fresh catalyst and ligand after 7 hours from the start of synthesis (entry 5), lowered yield of Compound 2c. Similarly, using a non-nucleophilic base, such as sodium hydride, in place of the nucleophilc base potassium t-butoxide decreased the yield of Compound 2c when all other reaction conditions were kept constant. See entries 6 and 2 respectively. The data in Table 3 indicate that increasing the reaction temperature, however, increases the yield of Compound 2c.

TABLE 3

Optimization of Reaction Conditions

| Entry | Conditions | Results |
|---|---|---|
| 1 | 1.05 eq. of naphthylamine, 1.2 eq t-BuOK, 1 mol % Pd(OAc)₂, 1.5 mol % BINAP, toluene, reflux | 24% |
| 2 | 1.05 eq. of naphthylamine, 1.2 eq t-BuOK, 1 mol % Pd(OAc)₂, 1.5 mol % BINAP, xylenes, reflux | 32% |
| 3 | 1.05 eq. of naphthylamine, 1.2 eq t-BuOK, 1 mol % Pd(OAc)₂, 1.5 mol % BINAP, benzene, reflux | 24% |

TABLE 3-continued

Optimization of Reaction Conditions

| Entry | Conditions | Results |
|---|---|---|
| 4 | 1.05 eq. of naphthylamine, 1.2 eq t-BuOK, 10 mol % Pd(OAc)$_2$, 15 mol % BINAP, toluene, reflux | 19% |
| 5 | 1.05 eq. of naphthylamine, 1.2 eq t-BuOK, 1 mol % Pd(OAc)$_2$, 1.5 mol % BINAP, xylenes, reflux More Pd(OAc)$_2$ and BINAP were added after 7 h | 14% |
| 6 | 1.05 eq. of naphthylamine, 1.2 eq NaH, 1 mol % Pd(OAc)$_2$, 1.5 mol % BINAP, xylenes, reflux | 17% |
| 7 | 1.05 eq. of naphthylamine, 1.2 eq t-BuOK, 1 mol % Pd(OAc)$_2$, 1.5 mol % BINAP, dry xylenes, reflux | 33% (44%)* + SM 31% |

Scheme 3:

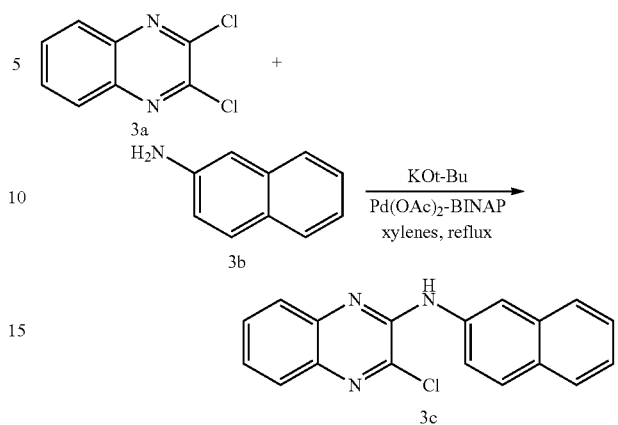

Scheme 4:

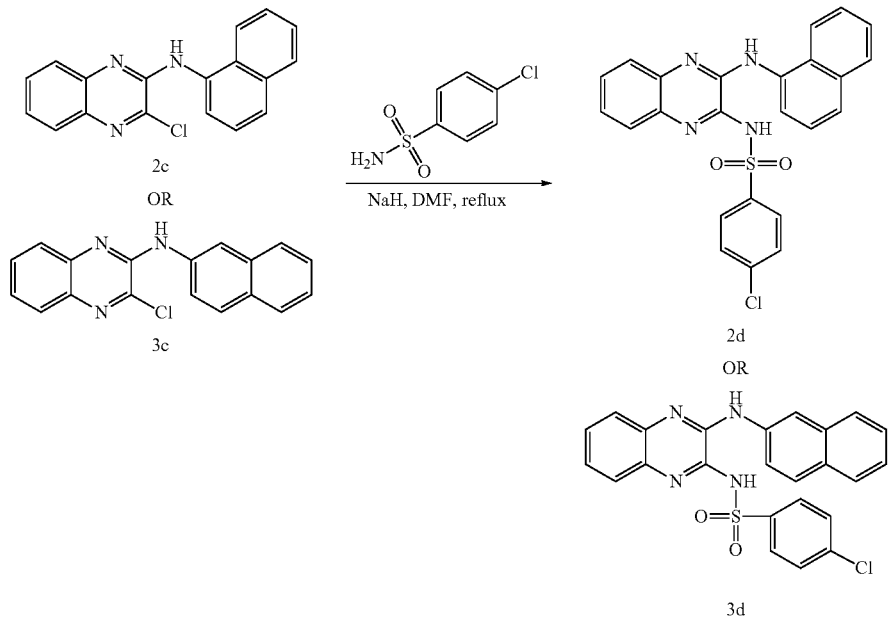

TABLE 3-continued

Optimization of Reaction Conditions

| Entry | Conditions | Results |
|---|---|---|
| 8 | 1.05 eq. of naphthylamine, 1.2 eq t-BuOK, 1 mol % Pd(OAc)$_2$, 1.5 mol % BINAP, 1,4-Dioxane, reflux | traces |

*yield based on recovery of starting material (2,3-dichloroquinoxaline 2 a).

A similar synthetic route was followed to introduce a 2-aminonaphthyl group in to the 2,3-dichloroquinoxaline scaffold, (Scheme 3). The overall yield for the product Compound 3c (3-chloro-(N-naphthylen-1-yl)-2-aminoquinoxaline) is lower, however. As illustrated in Scheme 4, compounds 2c or 3c upon further reaction with an appropriately substituted aryl sulfonamide results in a Formula I compound (Scheme 4).

The affinity of naphthyl quinoxaline derivatives for the Nef-Hck complex allows the use of the inventive compounds as anchors for protein targets associated with disease states. Typically, biotinylated quinoxaline derivatives are used in for this purpose. Schemes 5 and 6 illustrate different synthetic methodologies for making a biotinylated quinoxline derivative. As illustrated in this Scheme 5A, the chloroquinoxalinyl arylsulfonylamide is first reacted with a 4-aminophenoxynitrile (5-3) prepared separately from 4-aminophenol (5-1) and bromoacetonitrile (5-2). Reduction of the nitrile to the corresponding amine followed by reaction with biotin carboxylate gives the corresponding biotinylated derivative of quinoxalinyl 2-arylsulfonamide (Scheme 5A).

Alternatively, compound 5c also can be obtained by reacting 5a with 4-aminophenol, followed by the alkylation of the hydroxyl group with bromo acetonitrile to give 5-3, which upon reduction gives the desired product (5c), (Scheme 5B).

Scheme 5A:
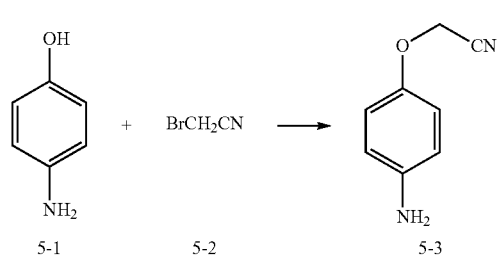
5-1    5-2    5-3
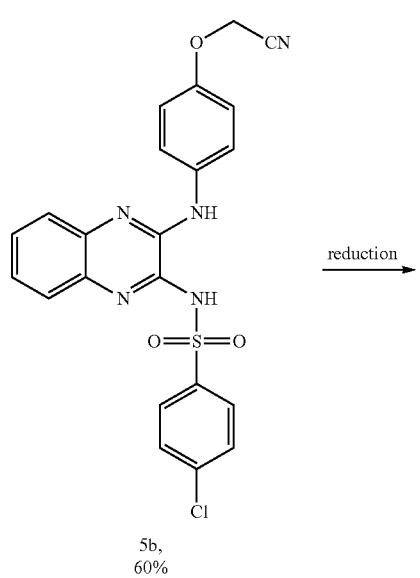
5b, 60%
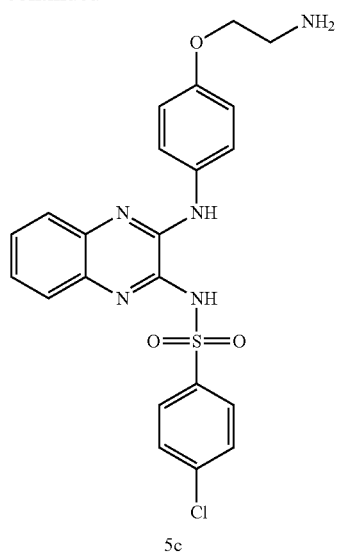 [SMILES: NCCOc1ccc(Nc2nc3ccccc3nc2NS(=O)(=O)c2ccc(Cl)cc2)cc1]
5c
Scheme 5B:
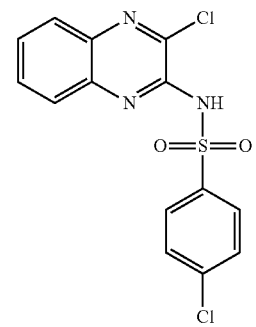
5-1    5a
5-4

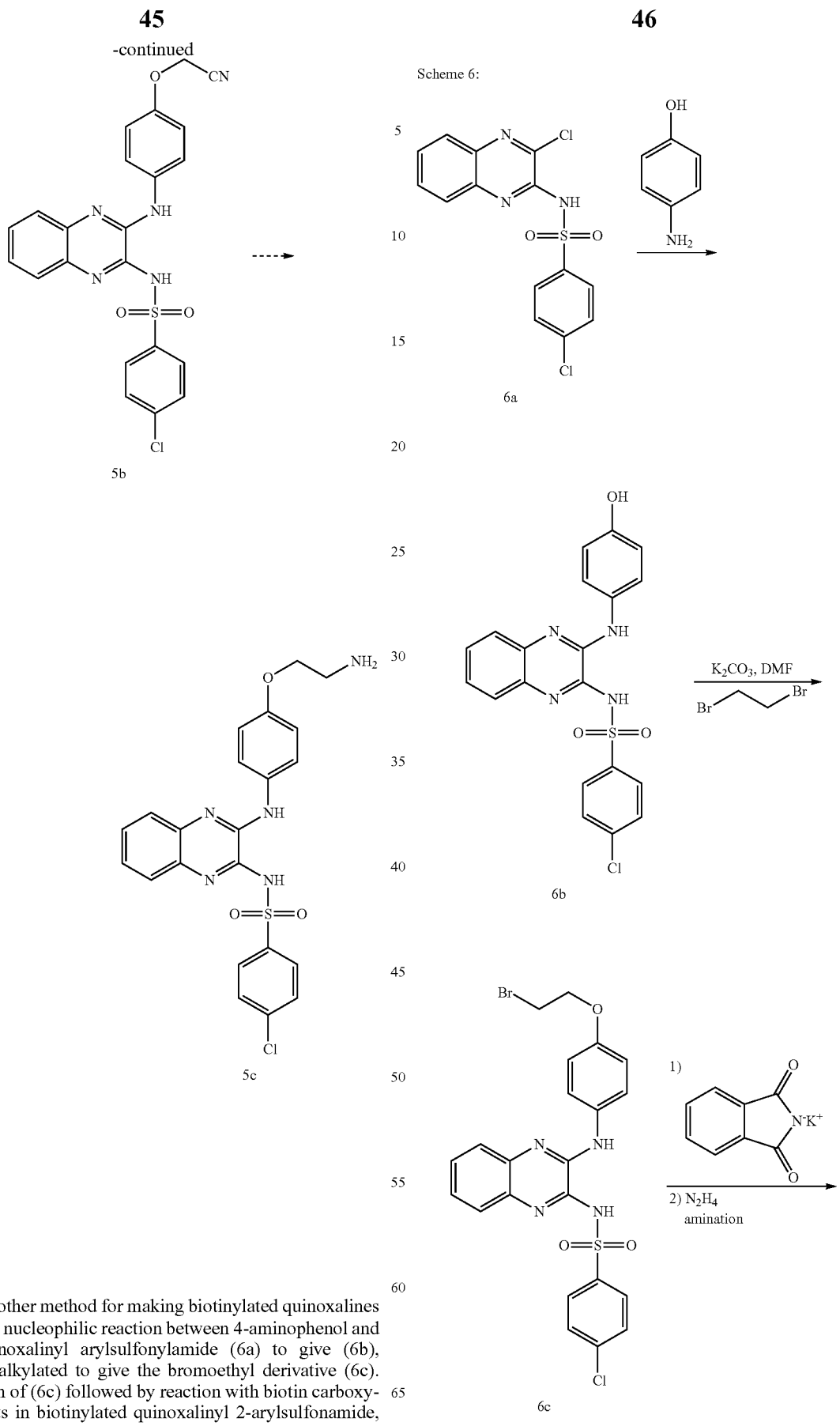
Still another method for making biotinylated quinoxalines involves a nucleophilic reaction between 4-aminophenol and chloroquinoxalinyl arylsulfonylamide (6a) to give (6b), which is alkylated to give the bromoethyl derivative (6c). Amination of (6c) followed by reaction with biotin carboxylate results in biotinylated quinoxalinyl 2-arylsulfonamide, (Scheme 6).

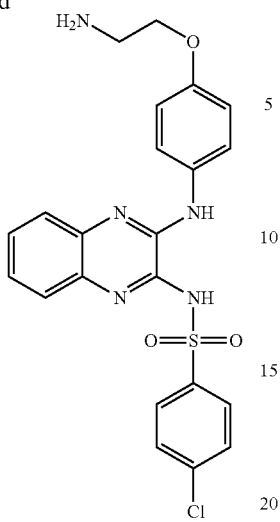

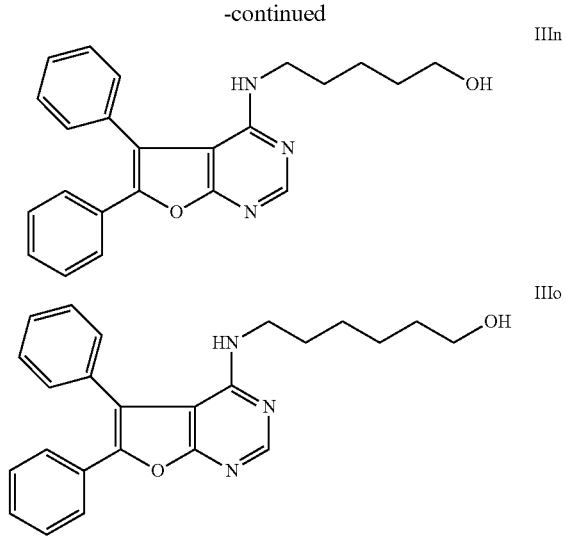

In some embodiments of the present invention contemplating compounds having the structure of Formula II, $R^{44}$, $R^{45}$, and $R^{46}$ are independently selected from the group consisting of hydrogen, halogen, and optionally substituted alkyl. In some embodiments, any one or more of $R^{44}$, $R^{45}$, and $R^{46}$ are optionally substituted alkyl.

Lead Compounds from Nef:SFK Kinase Activity in an In Vitro Assay System

The present invention also encompasses compounds of Formula III. Illustrative of compounds according to this scaffold are those represented by Formulae IIIL, IIIa, IIIm, IIIn, and IIIo:

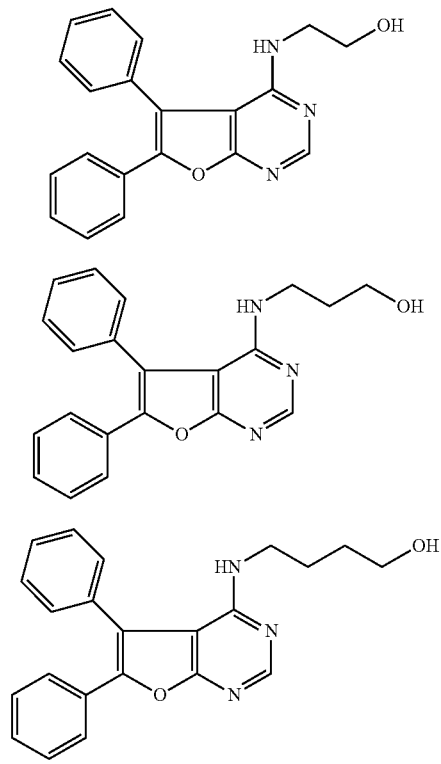

It has been found that the activity of the diphenylfuro derivatives is dependent on linker length as well as the chemical nature of the substituent ($R^{20}$) attached to the 4-amino group.

Representative examples of compounds according to this scaffold include diphenylfuro derivatives that are substituted with various heteroarylalkyl groups at $R^{20}$ and whose structures are shown below:

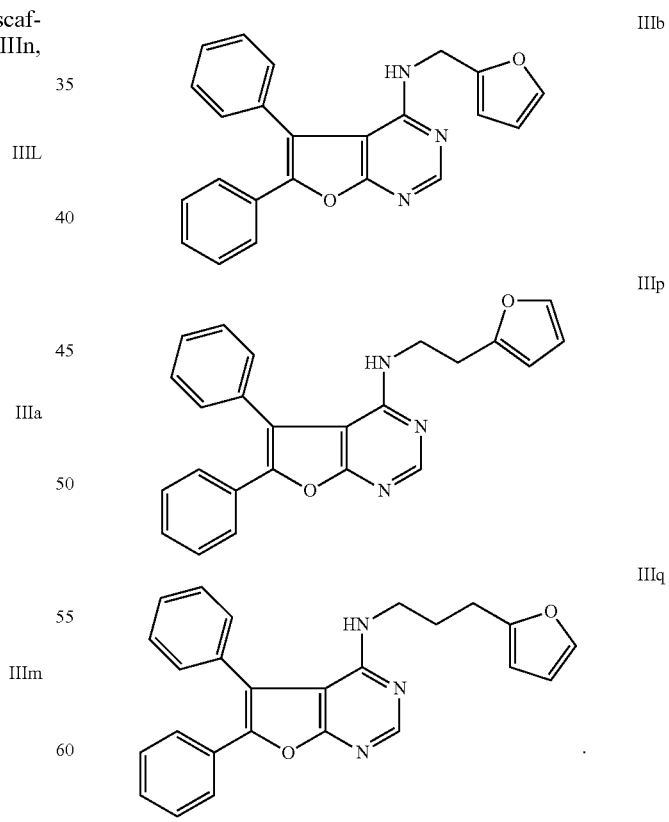

Alternatively, the present invention contemplates diphenylfuro derivatives in which the phenyl groups at positions $Cy^3$ and/or $Cy^4$ on the furan ring are replaced by an optionally substituted heteroaryl group. As shown below, one or both phenyl rings can be replaced by a furan ring.
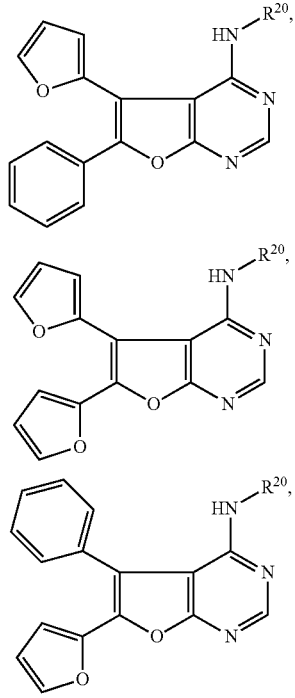
Illustrative compounds are shown below in which either Cy³ or Cy⁴ or both groups are heteroaryl.
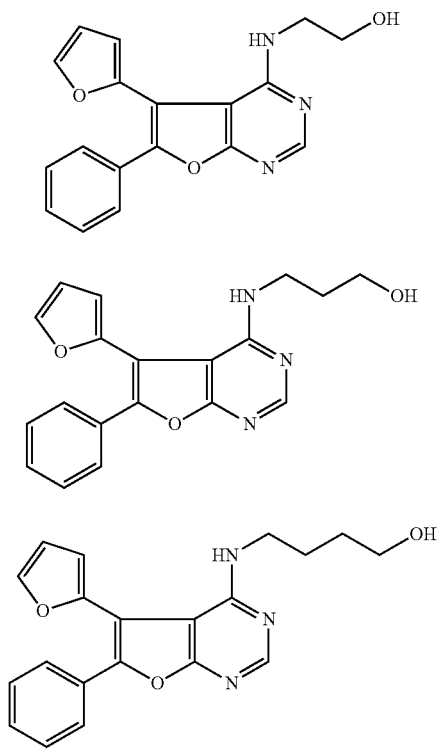
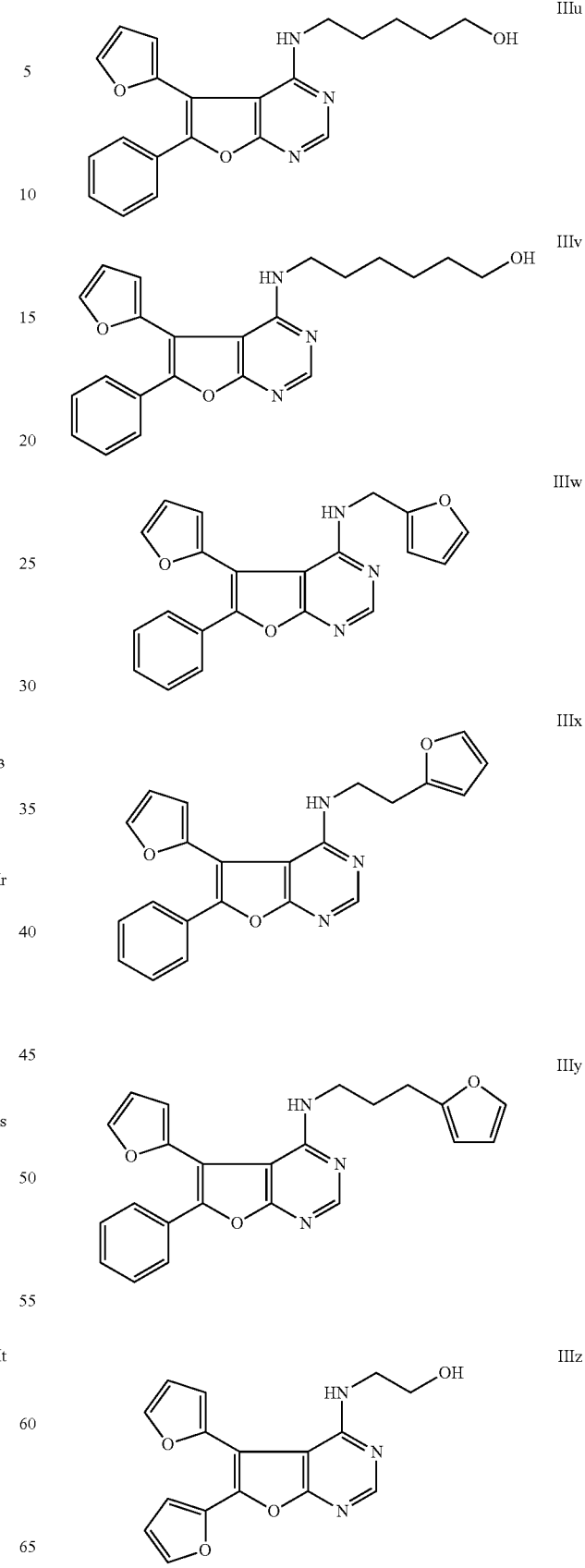

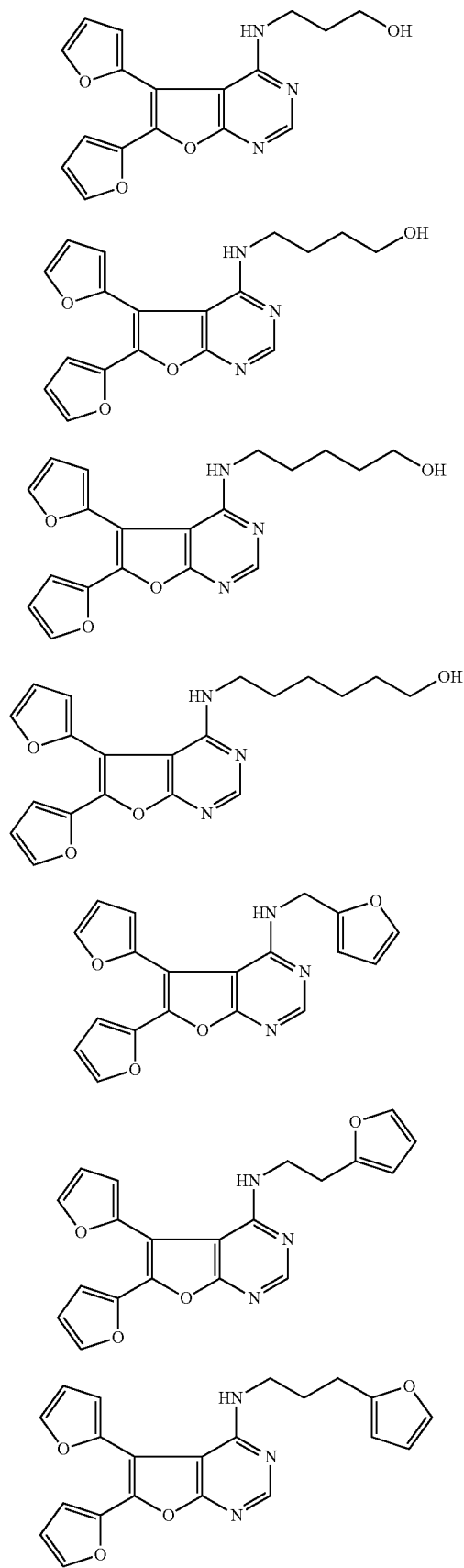
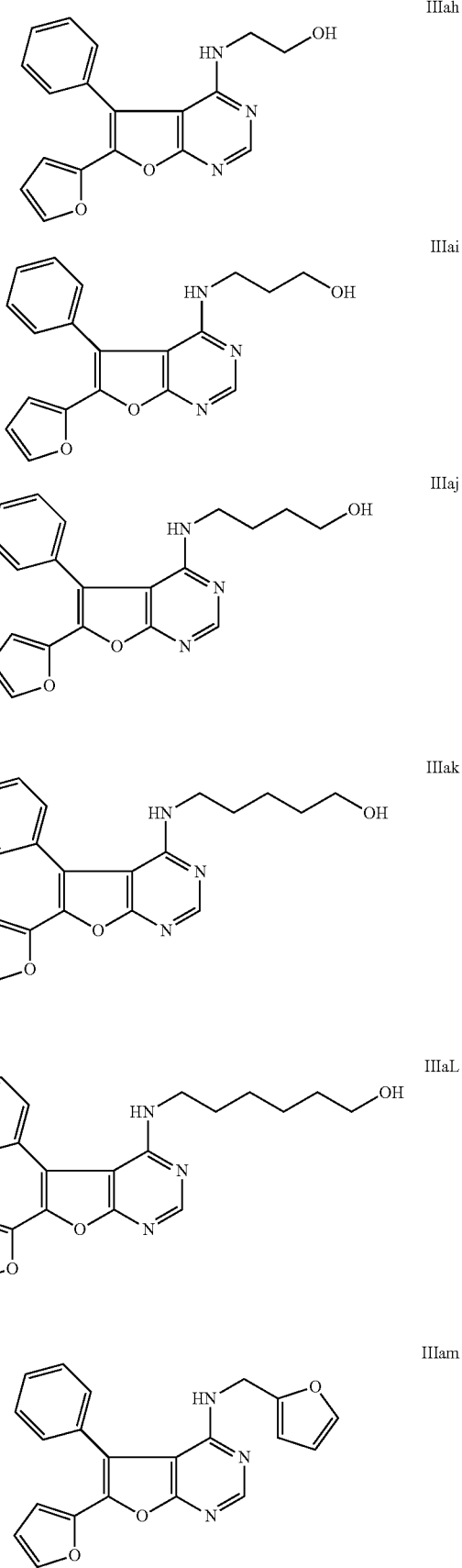

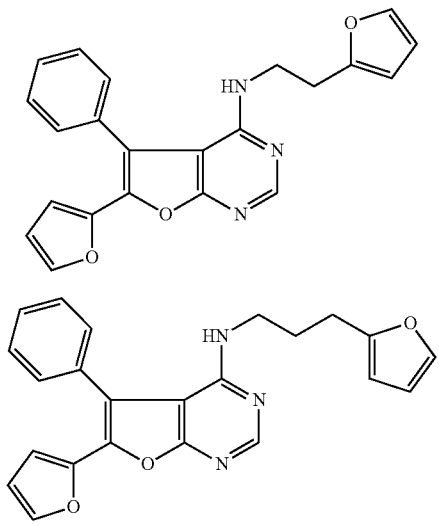

In some embodiments of the present invention contemplating compounds of Formula IV, $L^1$ is alkylene, preferably methylene, ethylene or propylene, $R^{30}$ is optionally substituted aryl, and $R^{31}$ is optionally substituted alkyl.

In some embodiments of the present invention contemplating compounds of Formula V, $R^{51}$ is —$NR^{52}R^{53}$, $R^{52}$ and $R^{53}$ are optionally substituted alkyl, and $Cy^5$ is optionally substituted aryl.

Therapeutic Uses of Compounds of Formulae I-V

Compounds of this invention inhibit the Nef-SFK complex, which plays an important role in HIV-1 replication. In one aspect, therefore, the inventive compounds can be used for treating HIV-1 infection in a subject. In the context of this invention, the terms "treat", "treating" and "treatment" refer to the amelioration or eradication of a disease or symptoms associated with a disease. In certain embodiments, such terms refer to minimizing the spread or worsening of the disease resulting from the administration of compounds in accordance with this invention to a subject with such a disease.

Accordingly, the invention provides formulations of compounds belonging to Formulae I-V, respectively, as potent selective inhibitors of viral replication. Such inhibition is reflected in various biochemical indicia, such as a decrease in kinase activity, a lowering of p24 gag protein levels released from HIV infected cells in culture, and an increase in CD4 positive T-cells.

The amount of compound that results in greater than about 95% decrease in one or more indicia of viral replication in vitro can be used in determining an effective dose ("therapeutic dose") in vivo, pursuant to conventional pharmaceutical practice. Thus, a pharmaceutical formulation that contains an amount of compound that results in blood concentrations equivalent to those documented here, such as an amount that produce greater than about 95% decrease in p24 levels in vitro, can be a reasonable starting point for dose-response studies of viral inhibition in vivo. The results from such studies can readily inform the production of a formulation that exhibits the desired therapeutic effect.

Compounds according to this invention, can be formulated with a pharmaceutically acceptable carrier, either as a prodrug or as a pharmaceutically acceptable salt, solvate, stereoisomer, or tautomer. For Formula I compounds, the polar amino and sulfonamide groups can promote hydrophilic interactions, such as hydrogen bonding with conventional aqueous carrier solvents, such as saline used in conventional formulations. On the other hand, derivatives that do not readily dissolve in an aqueous medium, can be formulated by the addition to the aqueous medium, pharmaceutically acceptable hydrophobic solvents, such as poly-alkylene glycol gelatin, gum arabic, lactose, starch, petroleum jelly and vegetable oil. By the same token, aqueous carriers can be used to formulate the hydrophilic Formulae III compounds. Additional excipients, such as flavoring agents, preservatives, stabilizers, emulsifying agents, buffers and the like may be added in accordance with accepted practices of pharmaceutical formulation.

A formulation of a compound of this invention can be administered intravenously, intraperitoneally, orally, bucally, or by parenteral administration. As the compounds described here are believed to have a mechanism of action analogous to clinically established, small-molecule protein-tyrosine kinase inhibitors, such as imatinib, dasatinib, and gefitinib, it should be possible to produce orally active formulations. Alternatively, compounds of the invention could be administered by other routes. Because the compounds target intracellular Nef-activated kinases in HIV-infected host cells, any route of administration resulting in sustained blood concentrations sufficient to penetrate such cells should produce a therapeutic benefit. HIV target cells include CD4+ T-cells, macrophages, and other CD4+ cells derived from them.

For oral administration, particularly suitable are tablets, dragees or capsules having talc and/or carbohydrate carrier binder or the like, the carrier could be lactose and/or corn starch and/or potato starch. A syrup, elixir or the like could be used when a sweetened vehicle is desired.

Synthesis

1. Synthesis of Quinoxaline Derivatives

The synthesis of all compounds was performed under nitrogen atmosphere. Commercially available precursors, solvents and reagents (Aldrich) were used without additional purification. Liquid chromatography-mass spectra (HPLC/MS) were obtained on an Applied Biosystems API 2000 instrument using electrospray ionization after HPLC separation on a Shimadzu system with UV detection using a C18 column and a gradient of $H_2O/CH_3CN$, both containing 0.1% $CH_3CO_2H$. High resolution mass spectra were obtained using matrix-assisted laser desorption ionization (MALDI) from 4-cyano-α-hydroxycinnamic acid matrix on 4700 and 4800 Applied Biosystems MALDI time-of-flight mass spectrometers. $^1H$ and $^{13}C$ NMR spectra were recorded on a Bruker Avance II 600 MHz spectrometer using deuterated solvents; chemical shifts are given in ppm and are referenced to residual solvent signal(s).

4-Chloro-N-(3-chloro-quinoxalin-2-yl)-benzenesulfonamide

To a solution of 4-Chlorobenzenesulfonamide (1.92 g, 10 mmol) in anhydrous DMF (50 mL) was added solid potassium carbonate (1.38 g, 10 mmol) in one portion. The reaction mixture was stirred for 10 minutes, followed by the addition of 2,3-dichloroquinoxaline (1.99 g, 10 mmol). Heating the resultant mixture under reflux conditions in an atmosphere of $N_2$ for 2.5 h gave the desired product. The progress of the reaction was monitored by TLC using, hexanes/EtOAc 3:1. After cooling the reaction mixture is slowly added to a vigorously stirred aqueous solution of AcOH (1%, 500 mL). The desired product precipitates as grey crystals, which are filtered and dried overnight in desiccator. Yield 2.32 g, 66%;

$R_f$=0.7 (hexanes/EtOAc 1:1); HPLC/MS: [M+H]+ m/z 354. $^1$H NMR: (DMSO-d6, 600 MHz) 7.68 (t, J=7.8 Hz, 1H), 7.72 (d, J=8.4 Hz, 2H), 7.78 (td, J=7.8 Hz, J=1.2 Hz, 1H), 7.89 (d, J=8.4 Hz, 2H), 8.19 (d, J=8.4 Hz, 2H).

4-Chloro-N-[3-(2,3-dihydro-benzo[1,4]dioxin-6-ylamino)-quinoxalin-2-yl]-benzenesulfonamide A solution of 4-Chloro-N-(3-chloro-quinoxalin-2-yl)-benzenesulfonamide (354 mg, 1 mmol) in xylenes (20 mL) was treated with 6-amino-1,4-benzodioxane (2 mmol, 246 μL), and the reaction mixture was refluxed under $N_2$ for 5 h. Removal of the solvent in vacuo gave the desired product which was further purified by column chromatography (hexanes/EtOAc 9:1) to give yellow crystals. MP=257-258° C., Yield 61%, TLC-$R_f$=0.3 (hexanes/EtOAc 3:1), HPLC/MS: [M+H]+ m/z 469. $^1$H NMR (CDCl$_3$, 600 MHz): δ 4.31 (m, 2H), 6.88 (d, J=9.0 Hz, 1H), 7.15 (dd, J=9.0 Hz, 2.4 Hz, 1H), 7.29 (dd, J=1.2 Hz, 1H), 7.36 (td, J=7.8 Hz, 1.2 Hz, 1H), 7.42 (td, J=7.8 Hz, 1.2 Hz, 1H), 7.53 (d, J=9 Hz, 2H), 7.70 (m, 2H), 7.98 (d, J=8.4 Hz, 2H), 8.19 (br.s, 1H), 11.88 (br.s, 1H). $^{13}$C NMR (CDCl$_3$, 150 MHz): δ 64.34, 64.53, 109.36, 113.54, 116.18, 117.28, 124.16, 125.87, 126.60, 126.81, 127.89, 129.38, 131.99, 134.18, 139.41, 140.14, 140.28, 141.24, 143.43, 144.08. HRMS: Calcd. for $C_{22}H_{18}ClN_4O_4S$ [M+H]+ m/z 469.0732, Observed 469.0704.

4-Chloro-N-[3-(naphthalen-1-ylamino)-quinoxalin-2-yl]-benzenesulfonamide, (2d)

A solution of 4-Chlorophenyl sulfonamide (287.5 mg, 1.5 mmol) in anhydrous DMF (10 mL), was treated with sodium hydride (60 mg, 1.5 mmol, 60% suspension in mineral oil; in one portion). The reaction mixture was stirred in an inert atmosphere of nitrogen for 1 h, followed by the dropwise addition of an anhydrous DMF solution of 2c (5 mL). The resultant mixture was heated under reflux under nitrogen for 40 h., quenched with water (100 mL) and extracted with ethyl acetate (3×50 mL). The combined organic layers were dried over MgSO$_4$, and the solvent removed in vacuo to give a residue which upon washing with hot methanol (20 mL) gave compound 2d as yellow crystals. MP=262-265° C., Yield 74%. $^1$H NMR, (CDCl$_3$, 600 MHz): δ 7.34 (d, J=7.8 Hz, 1H), 7.37 (td, J=7.8 Hz, J=1.8 Hz, 1H), 7.42 (td, J=8.4 Hz, J=1.2 Hz, 1H), 7.52-7.59 (m, 4H), 7.68-7.73 (m, 2H), 7.88-7.94 (m, 2H), 8.04 (dd, J=8.4 Hz, 2H), 9.00 (br.s, 1H), 11.92 (br.s, 1H). $^{13}$C NMR (CDCl$_3$, 150 MHz): δ 116.20, 117.99, 120.17, 124.75, 125.79, 126.07, 126.21, 126.40, 126.64, 126.96, 127.79, 128.90, 129.39, 132.80, 134.03, 134.06, 139.40, 140.26, 141.37, 144.67. HRMS: Calcd. for $C_{24}H_{18}ClN_4O_2S$ [M+H]+ m/z 461.0834, Observed 461.0829.

(3-Chloro-quinoxalin-2-yl)-naphthalen-1-yl-amine, (2c)

BINAP (93.3 mg, 0.15 mmol) and palladium acetate (22.6 mg, 0.1 mmol) were dissolved in dry xylenes (50 mL) and stirred for 10 min in an inert atmosphere of nitrogen. 2,3-Dichloroquinoxaline (1.99 g, 10 mmol), 1-naphthylamine (1.50 g, 10.5 mmol) and potassium tert-butoxide (1.34 g, 12 mmol) were the added to the reaction mixture which was heated for 22 h under reflux. After cooling to room-temperature, the reaction mixture was filtered and inorganic precipitate washed with dichloromethane (3×50 mL). Removal of the solvent in vacuo results in a residue which was purified using silica gel chromatography (hexanes/EtOAc 9:1). Compound 2c was isolated as yellow-orange crystals, mp=157-159° C. Yield 33%. TLC $R_f$=0.45 (hexanes/EtOAc 3:1). HPLC/MS: [M+H]+ m/z 306. $^1$H NMR (CDCl$_3$, 600 MHz): δ 7.50 (td, J=7.2 Hz, 1.2 Hz, 1H), 7.56-7.63 (m, 4H), 7.74 (d, J=8.4 Hz, 1H), 7.78 (dd, J=8.4 Hz, 1.2 Hz, 1H), 7.89 (dd, J=8.4 Hz, 1.2 Hz, 1H), 7.90 (d, J=8.4 Hz, 1H), 7.99-8.04 (m, 2H), 8.54 (d, J=7.2 Hz, 1H). $^{13}$C NMR (CDCl$_3$, 150 MHz): δ 118.62, 120.31, 125.01, 125.85, 126.10, 126.26, 126.45, 126.74, 126.79, 127.89, 129.01, 130.42, 133.25, 134.26, 137.25, 138.12, 140.59, 145.71. HRMS: Calcd. for $C_{18}H_{13}ClN_3$ [M+H]+ m/z 306.0793, Observed 306.0786.

(3-Chloro-quinoxalin-2-yl)-naphthalen-2-yl-amine, (3c)

Orange crystals, MP=148-150° C. $R_f$=0.35 (hexanes/EtOAc 3:1). HPLC/MS: [M+H]+ m/z 306. $^1$H NMR (CDCl$_3$, 600 MHz): δ 7.44 (td, J=8.4 Hz, 1.2 Hz, 1H), 7.52 (td, J=7.8 Hz, 1.2 Hz, 2H), 7.64-7.68 (m, 2H), 7.71 (dd, J=9.0 Hz, 2.4 Hz, 1H), 7.83 (d, J=8.4 Hz, 1H), 7.85-7.93 (m, 4H), 8.64 (d, J=1.8 Hz, 1H). $^{13}$C NMR (CDCl$_3$, 150 MHz): δ 115.89, 120.30, 124.84, 126.30, 126.59, 126.69, 127.64, 127.66, 127.88, 128.73, 130.36, 130.44, 133.99, 135.95, 137.09, 137.73, 140.40, 144.87. HRMS: Calcd. for $C_{18}H_{13}ClN_3$ [M+H]+ m/z 306.0793, Observed 306.0777.

4-Chloro-N-[3-(naphthalen-2-ylamino)-quinoxalin-2-yl]-benzenesulfonamide, (3d)

Yellow crystals; HPLC/MS: [M+H]+ m/z 460. TLC $R_f$=0.25 (hexanes/EtOAc 3:1). MP=222-224° C. $^1$H NMR (CDCl$_3$, 600 MHz): δ 7.30 (d, J=8.4 Hz, 1H), 7.38 (t, J=7.8 Hz, 1H), 7.41 (t, J=7.2 Hz, 1H), 7.44 (t, J=7.8 Hz, 1H), 7.48 (t, J=8.4 Hz, 1H), 7.51 (d, J=8.4 Hz, 2H), 7.66 (dd, J=9.0 Hz, J=1.8 Hz, 1H), 7.79 (t, J=9.0 Hz, 2H), 7.82 (d, J=9.0 Hz, 1H), 7.84 (d, J=8.4 Hz, 1H), 7.97 (d, J=8.4 Hz, 2H), 8.48 (br.s., 1H), 8.69 (br.s., 1H), 11.92 (br.s., 1H). $^{13}$C NMR (CDCl$_3$, 150 MHz): δ 116.20, 120.20, 124.25, 124.91, 126.28, 126.54, 126.67, 126.95, 127.58, 127.67, 127.88, 128.71, 129.38, 130.35, 133.89, 134.00, 135.54, 139.45, 140.12, 141.25, 144.15. HRMS: Calcd. for $C_{24}H_{18}ClN_4O_2S$ [M+H]+ m/z 461.0834, Observed 461.0797.

4-Chloro-N-[3-(4-hydroxy-phenylamino)-quinoxalin-2-yl]-benzenesulfonamide, (5-4)

A solution of 4-aminophenol (22 mg, 0.2 mmol) in xylenes (2 mL), was treated with 4-chloro-N-(3-chloro-quinoxalin-2-yl)-benzenesulfonamide (35.4 mg, 0.1 mmol) in one portion. The reaction mixture was heated under reflux in an inert atmosphere of nitrogen for 25 h. Reaction progress was monitored by TLC. Upon completion of the reaction, the mixture was cooled, which resulted in compound 5-4 precipitating from the solution as red-yellow crystals. The crystals were filtered and washed with hot methanol (5 mL) and pentane (5×5 mL). Yield 60%, mp=298-301° C. TLC $R_f$=0.35 (hexanes/EtOAc 1:1). $^1$H NMR (DMSO-d6, 600 MHz): δ 6.75 (d, J=8.4 Hz, 2H), 7.30 (t, J=7.2 Hz, 1H), 7.35 (t, J=7.2 Hz, 1H), 7.66 (d, J=8.4 Hz, 2H), 7.69 (d, J=7.8 Hz, 2H), 7.89 (br.s, 1H), 8.11 (d, J=7.8 Hz, 2H), 8.81 (br.s, 1H), 9.30 (br.s, 1H), 12.29 (br.s, 1H). HPLC/MS: [M+H]+ m/z 426. HRMS: Calcd. [M+H]+ m/z 427.0632, Observed 427.0644.

(4-Amino-phenoxy)-acetonitrile, (5-3)

Cs$_2$CO$_3$ (1629 mg, 5 mmol) was added in one portion to a solution of 4-aminophenol (541 mg, 5 mmol) in acetonitrile (20 mL). The reaction mixture was stirred at room temperature for 30 min and cooled to 0° C. prior to the addition of a solution of bromoacetonitrile (313 µL, 5 mmol) in acetonitrile (10 mL) dropwise. After stirring at room temperature for 48 h (TLC control), the reaction mixture is filtered and the filtrate evaporated to dryness in vacuo. The residue obtained after solvent removal was purified by silica gel column chromatography (hexanes/EtOAc 1:1). The desired product was isolated as yellow-brown oil. Yield: 559 mg, 76%. TLC $R_f$=0.2 (hexanes/EtOAc 1:1). $^1$H NMR (CDCl$_3$, 600 MHz): δ 3.56 (br.s, 2H, NH$_2$), 4.66 (s, 2H, CH$_2$), 6.65 (d, J=8.4 Hz, 2H), 6.83 (d, J=8.4 Hz, 2H). $^{13}$C NMR (CDCl$_3$, 150 MHz): δ 55.28, 115.60, 116.25, 117.10, 142.42, 149.65. HRMS: Calcd. [M+H]$^+$ m/z 149.0715, Observed 149.0689.

4-Chloro-N-[3-(4-cyanomethoxy-phenylamino)-quinoxalin-2-yl]-benzene sulfonamide, (5b)

A solution of 4-aminophenoxy acetonitrile (430 mg, 2.9 mmol) in xylenes (25 mL) was treated with 4-chloro-N-(3-chloro-quinoxalin-2-yl)-benzenesulfonamide (514 mg, 1.45 mmol) in one portion. The reaction mixture was heated under reflux in an inert atmosphere of nitrogen for 30 h (TLC was used to monitor reaction progress). Upon completion of the reaction, the mixture was cooled, which caused the crude product to precipitate from solution as yellow crystals. Filtration of the crude, followed by washing with pentane (5×20 mL) gave the tiled compound. Yield 87%; mp=221-223° C. (decomp). TLC $R_f$=0.4 (hexanes/EtOAc 1:1). $^1$H NMR (CDCl$_3$, 600 MHz): δ 4.77 (s, 2H, CH$_2$), 7.01 (d, J=9.0 Hz, 2H), 7.28 (dd, J=7.8 Hz, J=1.2 Hz, 1H), 7.35 (td, J=8.4 Hz, J=1.2 Hz, 1H), 7.40 (td, J=7.8 Hz, J=1.2 Hz, 1H), 7.50 (d, J=9.0 Hz, 2H), 7.66 (dd, J=8.4 Hz, J=1.2 Hz, 1H), 7.85 (d, J=9.0 Hz, 2H), 7.94 (d, J=9.0 Hz, 2H), 8.26 (br.s, 1H), 11.88 (br.s, 1H). $^{13}$C NMR (CDCl$_3$, 150 MHz): δ 54.20, 115.12, 115.75, 116.24, 121.52, 124.26, 126.19, 126.72, 126.80, 127.89, 129.42, 133.71, 133.96, 139.51, 140.13, 141.18, 144.13, 152.79. HPLC/MS [M+H]$^+$ m/z 466. HRMS: Calcd. [M+H]$^+$ m/z 466.0741, Observed 466.0753.

2. Synthesis of Diphenylfuropyrimidine-4-amino Derivatives:

Scheme 7 illustrates a versatile synthetic route for incorporating different substituent groups at the 4-amino position of the furopyrimidine scaffold. Synthesis of the bisphenyl furopyrimidine scaffold starts via the condensation of benzoin (7a) and malononitrile (7b) to give the di-substituted cyanofuran (7c) as product. Treatment of the cyanofuran with formamide in the presence of trace levels of acetic acid gave the 4-amino furopyrimidine compound (7d). The 4-amino group can then be alkylated to give different derivatives, including compound IIIa.

Scheme 7:

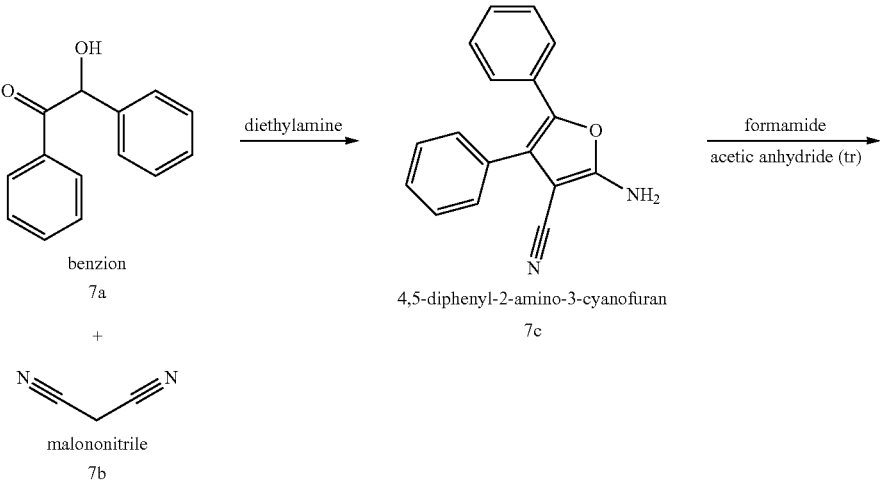

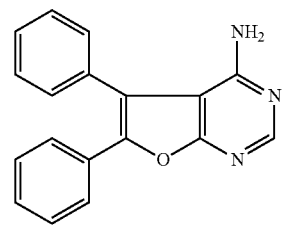

5,6-diphenylfuro[2,3-d]pyrimidin-4-amine
(DFP-4-amine)
7d

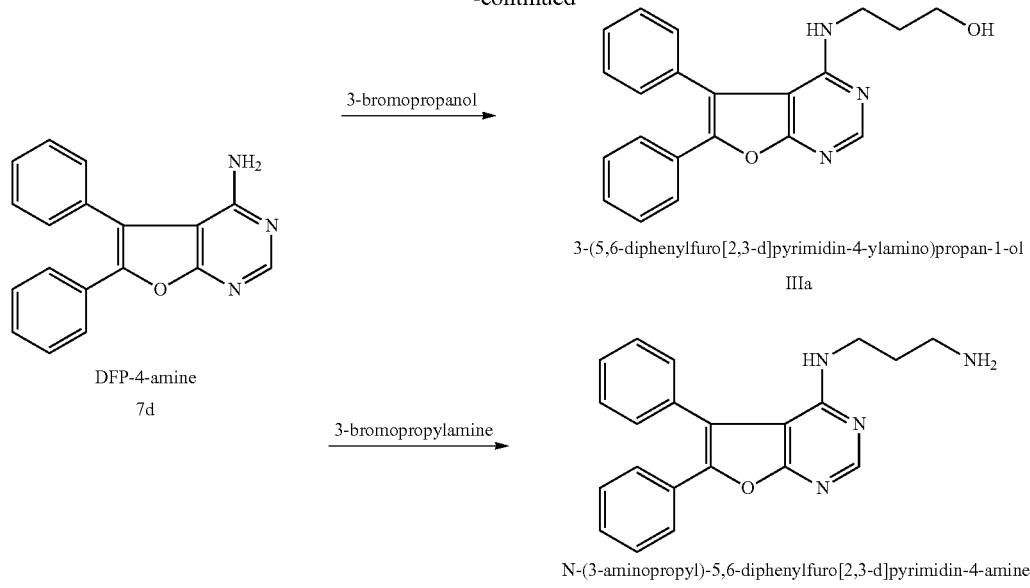
To illustrate the versatility of this synthetic approach, the following exemplary furoquinoxaline derivatives were synthesized as shown in Scheme 8.
Scheme 8:
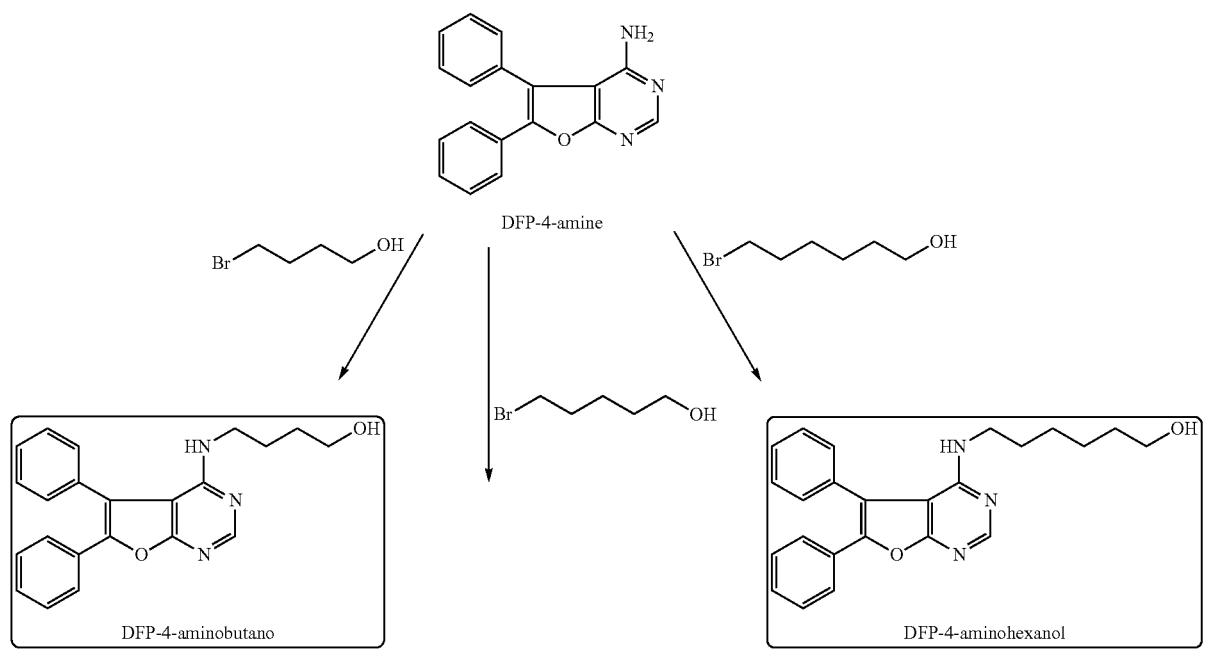

-continued

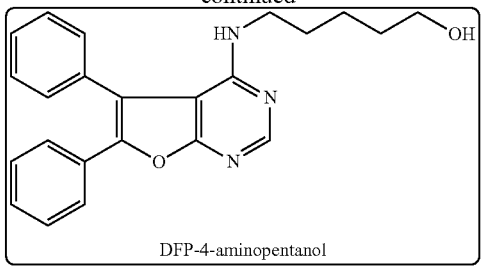
DFP-4-aminopentanol

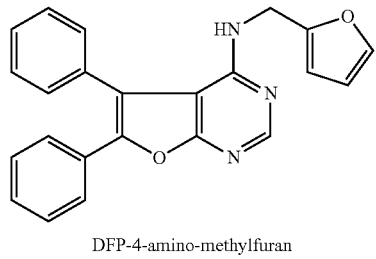
DFP-4-amino-methylfuran

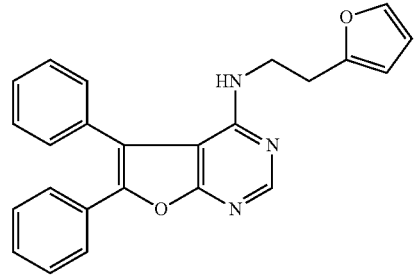
DFP-4-amino-ethylfuran

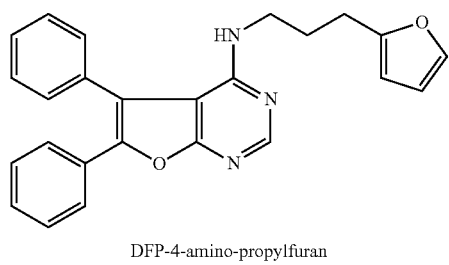
DFP-4-amino-propylfuran

EXAMPLES

Example 1

Recombinant Protein Expression and Purification

Hck-YEEI (SEQ ID NO: 4) and Nef were expressed in Sf9 insect cells and purified as described, for example, by Trible, 2006, Id.

Example 2

In Vitro Kinase Assay and Chemical Library Screening

Protein-tyrosine kinase assays were performed in 384-well plates using the Z'-LYTET™ kinase assay system and "Tyr 2 peptide" substrate (Invitrogen, Carlsbad, Calif.) as described by Trible et al. (Id.) Chemical libraries were purchased from Chempiv, Inc. (San Diego, Calif.) and include a kinase-directed library (2500 compounds), a phosphatase directed library (2500 compounds) and a diversity set (5040 compounds). Library screens were conducted 384-well plates in a final volume of 10 µl per well. Compounds were added to each well (10 µM final), followed by a preformed complex of Hck-YEEI (SEQ ID NO: 4) (10 ng/well) and Nef (1:20 molar ratio) plus the substrate peptide (2 µM). Reactions were initiated by the addition of ATP (50 µM final) and incubated at room temperature for 35 minutes. Reactions were developed and terminated per manufacturer's protocol, and with fluorescence ratios calculated as described (Trible et al., Id.)

Example 3

HIV Replication Assay

HIV-1 replication assays were conducted using HIV-1 strain NL4-3, a strain that is very similar, as known to those of skill in the art, in sequence to the SF2 allele used in the yeast assays and that strongly activates Hck-YEEI (SEQ ID NO: 4). Virus stocks were prepared by transfection of the recombinant viral genome into 293T cells. Viral replication was monitored in the U87MG astroglioma cell line expressing CD4 and CXCR4 (Salvatori, F. & Scarlatti, G., 2001, *AIDS Res. Hum. Retroviruses* 17: 925-35; Trkola, A. et al., 1998, *J. Virol.* 782:1876-1885). Viral replication was monitored by measuring p24 protein levels in the culture supernatant 4 days after infection by standard ELISA-based techniques. Test compounds were added to the culture 30 min prior to infection with HIV, and DMSO was used as the carrier solvent at a final concentration of 0.1%.

Example 4

Yeast Expression Vectors

Coding sequences for human Csk and Hck as well as HIV-1 Nef (SF2 strain) were modified by PCR to introduce a yeast translation initiation sequence (AATA) immediately 5' to the ATG start codon. The coding sequence for Hck was subcloned downstream of the Gal10 promoter in the pYC2/CT vector (Invitrogen), which carries the CEN6/ARSH4 sequence for low-copy replication. The Csk and Nef coding sequences were subcloned downstream of the Gal1 and Gal10 promoters, respectively, in the yeast expression vector pESC-Trp (Stratagene, San Diego, Calif.). The coding sequence of the wild-type Hck tail (YQQQP, residues 500-504 of SEQ ID NO: 3) was modified by PCR to encode the high-affinity SH2-binding sequence, YEEIP (residues 500-504 of SEQ ID NO: 4), as described (Lerner, E. C. & Smithgall, T. E., Nat. Struct. Biol., 2002, 9:365-369; Schindler, T., et al., 1999, *Mol. Cell* 3:639-648). The Nef-PA mutant, in which prolines 72 and 75 are replaced with alanines, has also been described (Briggs, S. D., et al., 1997, *J. Biol. Chem.* 272:17899-17902).

Example 5

Yeast Growth Suppression Assay

*S. cerevisiae* strain YPH 499 (Stratagene) was co-transformed with pESC-Ura (or pYC2/CT) and pESC-Trp plasmids containing the genes of interest via electroporation (BioRad Gene Pulser II, Hercules, Calif.). Yeast were selected for three days at 30° C. on standard synthetic drop-out plates lacking uracil and tryptophan (SD/-U-T) with glucose as the sole carbon source to repress protein expression. Positive transformants were grown in liquid SD/-U-T medium plus glucose, normalized to $OD_{600nm}=0.2$ in water, and then spotted in four-fold dilutions onto SD/-U-T agar plates containing galactose as the sole carbon source to induce protein expression. Duplicate plates containing glucose were also prepared to control for yeast loading. Plates were incubated for three days at 30° C. and imaged on a flatbed scanner. Yeast patches appear as dark spots against the translucent agar background. All growth suppression assays were repeated at least three times starting with randomly selected independent transformed clones and produced comparable results. For the liquid growth assay, yeast strain W303a was co-transformed with the required plasmids, seeded at an initial density of $OD_{600nm}=0.05$ units in SD/-U-T medium, and incubated for 21 h at 30° C. The control inhibitor A-419259 (Calderwood, D. J., et al., 2002, *Bioorg. Med. Chem. Lett.* 12:1683-1686) was added with DMSO as carrier solvent to a final concentration of 0.1%.

Example 6

Immunoblotting

Aliquots of yeast cultures used for the spot assay were grown in SD/-U-T medium plus galactose for 18 h. Cells were pelleted, treated with 0.1 N NaOH for 5 min at room temperature (Kushnirov, V. V., 2000, *Yeast* 16:857-60), and normalized with SDS-PAGE sample buffer to 0.02 $OD_{600nm}$ units per μL. Aliquots of each lysate (0.2 $OD_{600nm}$ units) were separated via SDS-PAGE, transferred to PVDF membranes, and probed for protein phosphotyrosine content with a combination of the anti-phosphotyrosine antibodies PY99 (Santa Cruz Biotechnology, Santa Cruz, Calif.) and PY20 (Transduction Laboratories, Lexington, Ky.). Immunoblots were also performed with antibodies to Csk (C-20; Santa Cruz), Hck (N-30; Santa Cruz), actin (MAB1501; Chemicon International) and Nef (monoclonal Hyb 6.2; NIH AIDS Research and Reference Reagent Program).

Example 7

Yeast Inhibitor Screen

Yeast strain W303a was co-transformed with Hck-YEEI (SE0 ID NO: 4) and Nef expression plasmids and grown to an $OD_{600nm}$ of 0.05. Cells (100 μL) were plated in duplicate wells of a 96-well plate in the presence of each compound from the Chempiv kinase-biased inhibitor library (Chempiv, Inc., San Diego, Calif.). All compounds were initially screened at 10 μM with 0.5% DMSO as carrier solvent. Control wells contained 0.5% DMSO to define the extent of growth arrest as well as cells transformed with Hck-YEEI (SEQ ID NO: 4) plus the Nef-2PA mutant to define maximum outgrowth. Each plate also contained wells with 5 μM A-419259 as a positive control for drug-mediated growth reversion. Cultures were incubated at 30° C., and the $OD_{60nm}$ was measured at 0 and 22 h. Those compounds that induced a 10% or greater increase in yeast growth relative to the DMSO control were further assayed in triplicate and compared against A-419259-mediated growth reversion. Compounds from this secondary screen that recovered yeast growth to at least 25% of that observed with A-419259 were obtained in powder form from the provider of the original library (Chempiv) and assayed a third time in triplicate at 1, 3, 10, and 30 μM in comparison with 5 μM A-419259.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

A person skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of the invention, syntheses thereof, various methods of administration, and/or various indications of disease or other condition. Thus, such additional embodiments are within the scope of the present invention and the following claims.

The invention illustratively described here suitably may be practiced in the absence of any element or elements, limitation or limitations not specifically disclosed herein. Thus, for example, in each instance herein any of the terms "comprising," "consisting essentially of" and "consisting of" may be replaced with either of the other two terms so as to provide additional embodiments of the invention. The terms and expressions that have been employed are used as terms of description and not of limitation, and there is no intention in the use of such terms and expressions of excluding any equivalents of the features shown and described or portions thereof, but it is recognized that various modifications are possible within the scope of the invention claimed. Accordingly, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

Thus, additional embodiments are within the scope of the invention and within the following claims.

Amino Acid Sequences

```
HIV-1 Nef (NCBI Locus CAA41585)
                                                                  SEQ ID NO: 1
   1 mggkwskssv vgwptvrerm rraepaadgv gaasrdlekh gaitssntaa tnaacawlea
  61 qeeeevgfpv tpqvplrpmt ykaavdlshf lkekgglegl ihsqrrqdil dlwiyhtqgy
 121 fpdwqnytpg pgvrypltfg wcyklvpvep dkveeankge ntsllhpvsl hgmddperev
 181 lewrfdsrla fhhvarelhp eyfknc Human CSK (NCBI Locus CAG46758)
                                                                  SEQ ID NO: 2
   1 msaiqaawps gteciakynf hgtaeqdlpf ckgdvltiva vtkdpnwyka knkvgregii
  61 panyvqkreg vkagtklslm pwfhgkitre qaerllyppe tglflvrest nypgdytlcv
 121 scdgkvehyr imyhasklsi deevyfenlm qlvehytsda dglctrlikp kvmegtvaaq
 181 defyrsgwal nmkelkllqt igkgefgdvm lgdyrgnkva vkciknata qaflaeasvm
 241 tqlrhsnlvq llgviveekg glyivteyma kgslvdylrs rgrsvlggdc llkfsldvce
 301 ameylegnnf vhrdlaarnv lvsednvakv sdfgltkeas stqdtgklpv kwtapealre
 361 kkfstksdvw sfgillweiy sfgrvpypri plkdvvprve kgykmdapdg cppavyevmk
 421 ncwhldaamr psflqlreql ehikthelhl Human Hck (NCBI Locus CAI19695)
                                                                  SEQ ID NO: 3
   1 mgcmkskflq vggntfskte tsasphcpvy vpdptstikp gpnshnsntp giregsedii
  61 vvalydyeai hhedlsfqkg dqmvvleesg ewwkarslat rkegyipsny varvdslete
 121 ewffkgisrk daerqllapg nmlgsfmird settkgsysl svrdydprqg dtvkhykirt
 181 ldnggfyisp rstfstlqel vdhykkgndg lcqklsvpcm sskpqkpwek daweipresl
 241 klekklgagq fgevwmatyn khtkvavktm kpgsmsveaf laeanvmktl qhdklvklha
 301 vvtkepiyii tefmakgsll dflksdegsk qplpklidfs aqiaegmafi eqrnyihrdl
 361 raanilvsas lvckiadfgl arviedneyt aregakfpik wtapeainfg sftiksdvws
 421 fgillmeivt ygripypgms npeviraler gyrmprpenc peelynimmr cwknrpeerp
 481 tfeyiqsvld dfytatesqy qqqp Human Hck-YEEI
                                                                  SEQ ID NO: 4
   1 mgcmkskflq vggntfskte tsasphcpvy vpdptstikp gpnshnsntp giregsedii
  61 vvalydyeai hhedlsfqkg dqmvvleesg ewwkarslat rkegyipsny varvdslete
 121 ewffkgisrk daerqllapg nmlgsfmird settkgsysl svrdydprqg dtvkhykirt
 181 ldnggfyisp rstfstlqel vdhykkgndg lcqklsvpcm sskpqkpwek daweipresl
 241 klekklgagq fgevwmatyn khtkvavktm kpgsmsveaf laeanvmktl qhdklvklha
 301 vvtkepiyii tefmakgsll dflksdegsk qplpklidfs aqiaegmafi eqrnyihrdl
 361 raanilvsas lvckiadfgl arviedneyt aregakfpik wtapeainfg sftiksdvws
 421 fgillmeivt ygripypgms npeviraler gyrmprpenc peelynimmr cwknrpeerp
 481 tfeyiqsvld dfytatesqy eeip
```

What is claimed is:

1. A method for treating HIV-1 in a subject in need thereof, comprising (a) identifying a subject infected with HIV-1 and then (b) administering to said subject a therapeutic dose of a Formula I compound

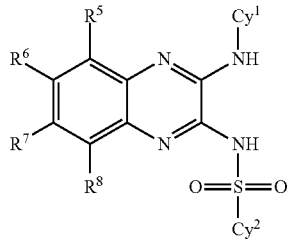

wherein $Cy^1$ is selected from the group consisting of aryl and heteroaryl, wherein the aryl or heteroaryl group is optionally substituted with one or more members selected from the group consisting of —OH, chloroacetyl halogen, sulfonic acid, nitro and —O-alkyl;

$Cy^2$ is an aryl optionally substituted with one or more members selected from the group consisting of halogen, alkyl, amino and —O-alkyl;

$R^5$, $R^6$, $R^7$, and $R^8$ are independently selected from the group consisting of hydrogen and —$OR^{11}$, and $R^{11}$ is selected from the group consisting of optionally substituted alkyl, optionally substituted cycloalkyl, optionally substituted heterocycloalkyl, optionally substituted aryl, optionally substituted arylalkyl, optionally substituted heteroaryl, and optionally substituted heteroarylalkyl.

2. The method according to claim 1, wherein said compound is selected from the group consisting of

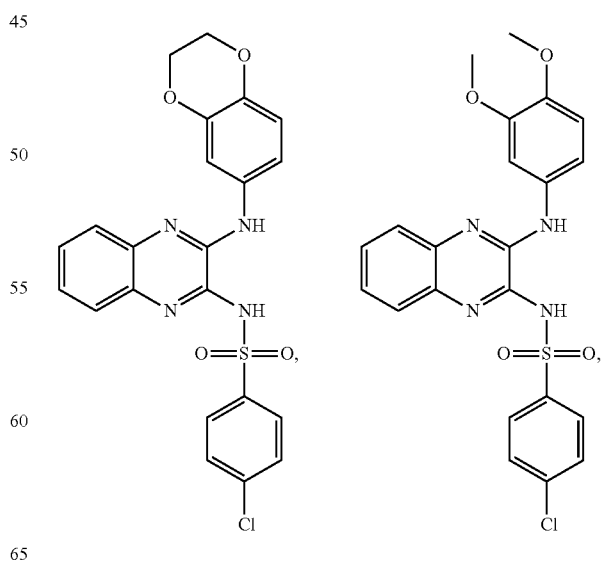

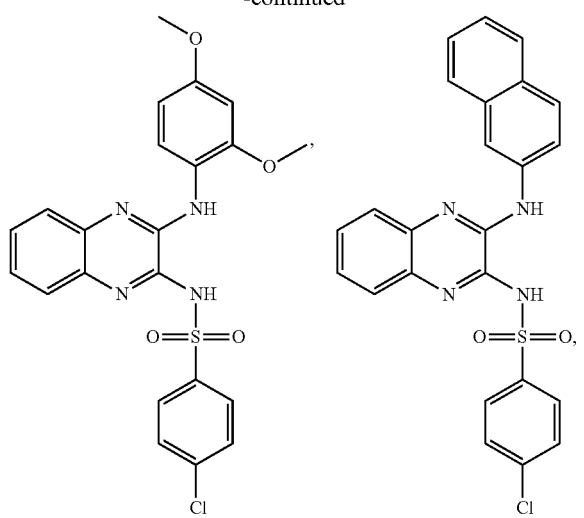
and
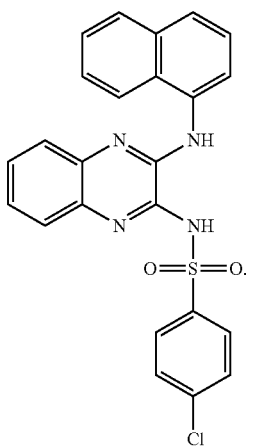
3. The method according to claim 1, wherein $Cy^1$ is selected from the group consisting of
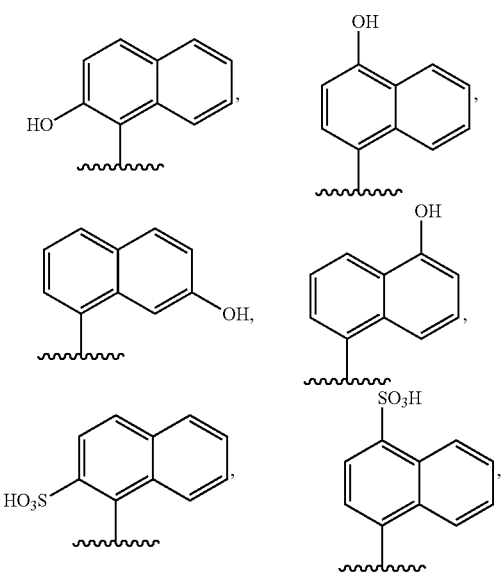
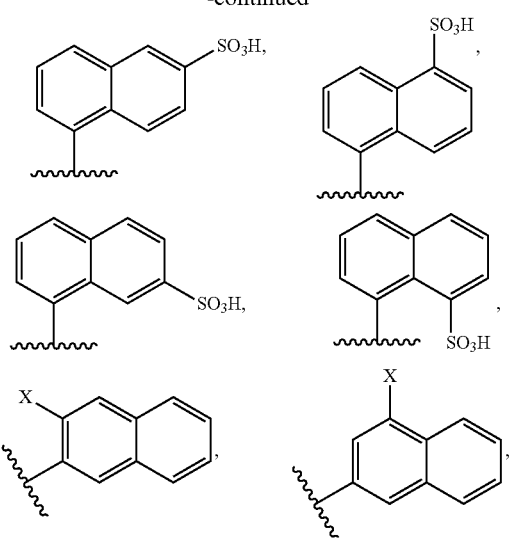
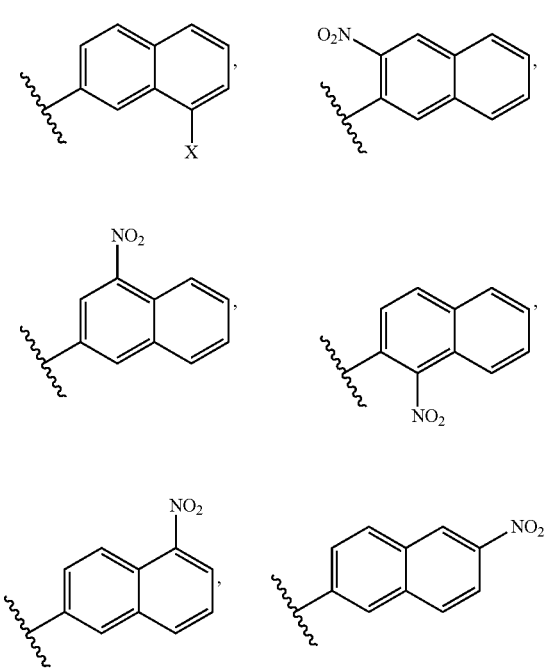

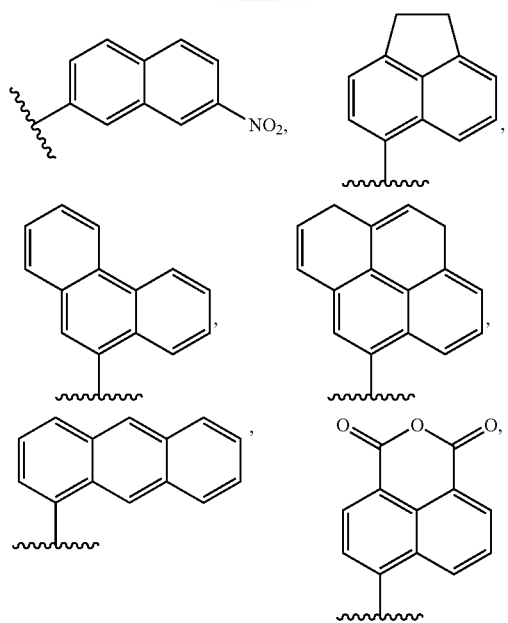
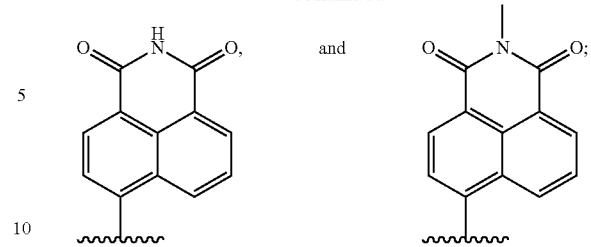
and
X is a halogen.
4. The method according to claim 3, wherein X is chlorine.
5. The method according to claim 1, wherein Cy¹ is
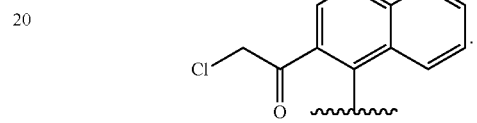
* * * * *

SEQUENCE LISTING

<160> NUMBER OF SEQ ID NOS: 6

<210> SEQ ID NO 1
<211> LENGTH: 206
<212> TYPE: PRT
<213> ORGANISM: Human immunodeficiency virus

<400> SEQUENCE: 1

Met Gly Gly Lys Trp Ser Lys Ser Ser Val Val Gly Trp Pro Thr Val
1               5                   10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Ala Cys Ala Trp Leu Glu Ala Gln Glu Glu Glu
    50                  55                  60

```
Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
            115                 120                 125

Pro Gly Pro Gly Val Arg Tyr Pro Leu Thr Phe Gly Trp Cys Tyr Lys
        130                 135                 140

Leu Val Pro Val Glu Pro Asp Lys Val Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205

<210> SEQ ID NO 2
<211> LENGTH: 450
<212> TYPE: PRT
<213> ORGANISM: Homo sapiens

<400> SEQUENCE: 2

Met Ser Ala Ile Gln Ala Ala Trp Pro Ser Gly Thr Glu Cys Ile Ala
  1               5                  10                  15

Lys Tyr Asn Phe His Gly Thr Ala Glu Gln Asp Leu Pro Phe Cys Lys
                 20                  25                  30

Gly Asp Val Leu Thr Ile Val Ala Val Thr Lys Asp Pro Asn Trp Tyr
             35                  40                  45

Lys Ala Lys Asn Lys Val Gly Arg Glu Gly Ile Ile Pro Ala Asn Tyr
         50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
                 85                  90                  95

Tyr Pro Pro Glu Thr Gly Leu Phe Leu Val Arg Glu Ser Thr Asn Tyr
            100                 105                 110

Pro Gly Asp Tyr Thr Leu Cys Val Ser Cys Asp Gly Lys Val Glu His
            115                 120                 125

Tyr Arg Ile Met Tyr His Ala Ser Lys Leu Ser Ile Asp Glu Glu Val
        130                 135                 140

Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
            180                 185                 190

Lys Glu Leu Lys Leu Leu Gln Thr Ile Gly Lys Gly Glu Phe Gly Asp
            195                 200                 205

Val Met Leu Gly Asp Tyr Arg Gly Asn Lys Val Ala Val Lys Cys Ile
        210                 215                 220

Lys Asn Asp Ala Thr Ala Gln Ala Phe Leu Ala Glu Ala Ser Val Met
225                 230                 235                 240
```

```
Thr Gln Leu Arg His Ser Asn Leu Val Gln Leu Leu Gly Val Ile Val
                245                 250                 255

Glu Glu Lys Gly Gly Leu Tyr Ile Val Thr Glu Tyr Met Ala Lys Gly
            260                 265                 270

Ser Leu Val Asp Tyr Leu Arg Ser Arg Gly Arg Ser Val Leu Gly Gly
        275                 280                 285

Asp Cys Leu Leu Lys Phe Ser Leu Asp Val Cys Glu Ala Met Glu Tyr
    290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Ser Thr Gln Asp Thr Gly Lys Leu Pro Val Lys Trp
            340                 345                 350

Thr Ala Pro Glu Ala Leu Arg Glu Lys Lys Phe Ser Thr Lys Ser Asp
        355                 360                 365

Val Trp Ser Phe Gly Ile Leu Leu Trp Glu Ile Tyr Ser Phe Gly Arg
    370                 375                 380

Val Pro Tyr Pro Arg Ile Pro Leu Lys Asp Val Val Pro Arg Val Glu
385                 390                 395                 400

Lys Gly Tyr Lys Met Asp Ala Pro Asp Gly Cys Pro Pro Ala Val Tyr
                405                 410                 415

Glu Val Met Lys Asn Cys Trp His Leu Asp Ala Ala Met Arg Pro Ser
            420                 425                 430

Phe Leu Gln Leu Arg Glu Gln Leu Glu His Ile Lys Thr His Glu Leu
        435                 440                 445

His Leu
    450

<210> SEQ ID NO 3
<211> LENGTH: 504
<212> TYPE: PRT
<213> ORGANISM: Homo sapiens

<400> SEQUENCE: 3

Met Gly Cys Met Lys Ser Lys Phe Leu Gln Val Gly Gly Asn Thr Phe
1               5                   10                  15

Ser Lys Thr Glu Thr Ser Ala Ser Pro His Cys Pro Val Tyr Val Pro
                20                  25                  30

Asp Pro Thr Ser Thr Ile Lys Pro Gly Pro Asn Ser His Asn Ser Asn
            35                  40                  45

Thr Pro Gly Ile Arg Glu Gly Ser Glu Asp Ile Ile Val Val Ala Leu
        50                  55                  60

Tyr Asp Tyr Glu Ala Ile His His Glu Asp Leu Ser Phe Gln Lys Gly
65                  70                  75                  80

Asp Gln Met Val Val Leu Glu Glu Ser Gly Glu Trp Trp Lys Ala Arg
                85                  90                  95

Ser Leu Ala Thr Arg Lys Glu Gly Tyr Ile Pro Ser Asn Tyr Val Ala
            100                 105                 110

Arg Val Asp Ser Leu Glu Thr Glu Glu Trp Phe Phe Lys Gly Ile Ser
        115                 120                 125

Arg Lys Asp Ala Glu Arg Gln Leu Leu Ala Pro Gly Asn Met Leu Gly
    130                 135                 140

Ser Phe Met Ile Arg Asp Ser Glu Thr Thr Lys Gly Ser Tyr Ser Leu
145                 150                 155                 160
```

Ser Val Arg Asp Tyr Asp Pro Arg Gln Gly Asp Thr Val Lys His Tyr
            165                 170                 175

Lys Ile Arg Thr Leu Asp Asn Gly Gly Phe Tyr Ile Ser Pro Arg Ser
            180                 185                 190

Thr Phe Ser Thr Leu Gln Glu Leu Val Asp His Tyr Lys Lys Gly Asn
            195                 200                 205

Asp Gly Leu Cys Gln Lys Leu Ser Val Pro Cys Met Ser Ser Lys Pro
210                 215                 220

Gln Lys Pro Trp Glu Lys Asp Ala Trp Glu Ile Pro Arg Glu Ser Leu
225                 230                 235                 240

Lys Leu Glu Lys Lys Leu Gly Ala Gly Gln Phe Gly Glu Val Trp Met
            245                 250                 255

Ala Thr Tyr Asn Lys His Thr Lys Val Ala Val Lys Thr Met Lys Pro
            260                 265                 270

Gly Ser Met Ser Val Glu Ala Phe Leu Ala Glu Ala Asn Val Met Lys
            275                 280                 285

Thr Leu Gln His Asp Lys Leu Val Lys Leu His Ala Val Val Thr Lys
            290                 295                 300

Glu Pro Ile Tyr Ile Ile Thr Glu Phe Met Ala Lys Gly Ser Leu Leu
305                 310                 315                 320

Asp Phe Leu Lys Ser Asp Glu Gly Ser Lys Gln Pro Leu Pro Lys Leu
            325                 330                 335

Ile Asp Phe Ser Ala Gln Ile Ala Glu Gly Met Ala Phe Ile Glu Gln
            340                 345                 350

Arg Asn Tyr Ile His Arg Asp Leu Arg Ala Ala Asn Ile Leu Val Ser
            355                 360                 365

Ala Ser Leu Val Cys Lys Ile Ala Asp Phe Gly Leu Ala Arg Val Ile
            370                 375                 380

Glu Asp Asn Glu Tyr Thr Ala Arg Glu Gly Ala Lys Phe Pro Ile Lys
385                 390                 395                 400

Trp Thr Ala Pro Glu Ala Ile Asn Phe Gly Ser Phe Thr Ile Lys Ser
            405                 410                 415

Asp Val Trp Ser Phe Gly Ile Leu Leu Met Glu Ile Val Thr Tyr Gly
            420                 425                 430

Arg Ile Pro Tyr Pro Gly Met Ser Asn Pro Glu Val Ile Arg Ala Leu
            435                 440                 445

Glu Arg Gly Tyr Arg Met Pro Arg Pro Glu Asn Cys Pro Glu Glu Leu
450                 455                 460

Tyr Asn Ile Met Met Arg Cys Trp Lys Asn Arg Pro Glu Glu Arg Pro
465                 470                 475                 480

Thr Phe Glu Tyr Ile Gln Ser Val Leu Asp Asp Phe Tyr Thr Ala Thr
            485                 490                 495

Glu Ser Gln Tyr Gln Gln Gln Pro
            500

<210> SEQ ID NO 4
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Cys Met Lys Ser Lys Phe Leu Gln Val Gly Gly Asn Thr Phe
1               5                   10                  15

-continued

```
Ser Lys Thr Glu Thr Ser Ala Ser Pro His Cys Pro Val Tyr Val Pro
             20                  25                  30
Asp Pro Thr Ser Thr Ile Lys Pro Gly Pro Asn Ser His Asn Ser Asn
             35                  40                  45
Thr Pro Gly Ile Arg Glu Gly Ser Glu Asp Ile Ile Val Val Ala Leu
 50                  55                  60
Tyr Asp Tyr Glu Ala Ile His His Glu Asp Leu Ser Phe Gln Lys Gly
 65                  70                  75                  80
Asp Gln Met Val Val Leu Glu Glu Ser Gly Glu Trp Trp Lys Ala Arg
                 85                  90                  95
Ser Leu Ala Thr Arg Lys Glu Gly Tyr Ile Pro Ser Asn Tyr Val Ala
                100                 105                 110
Arg Val Asp Ser Leu Glu Thr Glu Glu Trp Phe Phe Lys Gly Ile Ser
                115                 120                 125
Arg Lys Asp Ala Glu Arg Gln Leu Leu Ala Pro Gly Asn Met Leu Gly
                130                 135                 140
Ser Phe Met Ile Arg Asp Ser Glu Thr Thr Lys Gly Ser Tyr Ser Leu
145                 150                 155                 160
Ser Val Arg Asp Tyr Asp Pro Arg Gln Gly Asp Thr Val Lys His Tyr
                165                 170                 175
Lys Ile Arg Thr Leu Asp Asn Gly Gly Phe Tyr Ile Ser Pro Arg Ser
                180                 185                 190
Thr Phe Ser Thr Leu Gln Glu Leu Val Asp His Tyr Lys Lys Gly Asn
                195                 200                 205
Asp Gly Leu Cys Gln Lys Leu Ser Val Pro Cys Met Ser Ser Lys Pro
210                 215                 220
Gln Lys Pro Trp Glu Lys Asp Ala Trp Glu Ile Pro Arg Glu Ser Leu
225                 230                 235                 240
Lys Leu Glu Lys Lys Leu Gly Ala Gly Gln Phe Gly Glu Val Trp Met
                245                 250                 255
Ala Thr Tyr Asn Lys His Thr Lys Val Ala Val Lys Thr Met Lys Pro
                260                 265                 270
Gly Ser Met Ser Val Glu Ala Phe Leu Ala Glu Ala Asn Val Met Lys
                275                 280                 285
Thr Leu Gln His Asp Lys Leu Val Lys Leu His Ala Val Val Thr Lys
                290                 295                 300
Glu Pro Ile Tyr Ile Ile Thr Glu Phe Met Ala Lys Gly Ser Leu Leu
305                 310                 315                 320
Asp Phe Leu Lys Ser Asp Glu Gly Ser Lys Gln Pro Leu Pro Lys Leu
                325                 330                 335
Ile Asp Phe Ser Ala Gln Ile Ala Glu Gly Met Ala Phe Ile Glu Gln
                340                 345                 350
Arg Asn Tyr Ile His Arg Asp Leu Arg Ala Ala Asn Ile Leu Val Ser
                355                 360                 365
Ala Ser Leu Val Cys Lys Ile Ala Asp Phe Gly Leu Ala Arg Val Ile
                370                 375                 380
Glu Asp Asn Glu Tyr Thr Ala Arg Glu Gly Ala Lys Phe Pro Ile Lys
385                 390                 395                 400
Trp Thr Ala Pro Glu Ala Ile Asn Phe Gly Ser Phe Thr Ile Lys Ser
                405                 410                 415
Asp Val Trp Ser Phe Gly Ile Leu Leu Met Glu Ile Val Thr Tyr Gly
                420                 425                 430
Arg Ile Pro Tyr Pro Gly Met Ser Asn Pro Glu Val Ile Arg Ala Leu
                435                 440                 445
```

```
Glu Arg Gly Tyr Arg Met Pro Arg Pro Glu Asn Cys Pro Glu Glu Leu
    450                 455                 460
Tyr Asn Ile Met Met Arg Cys Trp Lys Asn Arg Pro Glu Glu Arg Pro
465                 470                 475                 480
Thr Phe Glu Tyr Ile Gln Ser Val Leu Asp Asp Phe Tyr Thr Ala Thr
                485                 490                 495
Glu Ser Gln Tyr Glu Glu Ile Pro
            500

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Glu Glu Ile
1

<210> SEQ ID NO 6
<211> LENGTH: 4
<212> TYPE: PRT
<213> ORGANISM: Homo sapiens

<400> SEQUENCE: 6

Tyr Gln Gln Gln
1
```